United States Patent
Chudzinski-Tavassi et al.

(10) Patent No.: US 12,187,785 B2
(45) Date of Patent: Jan. 7, 2025

(54) RECOMBINANT PROTEIN AND FRAGMENTS THEREOF, METHOD FOR PRODUCING SAID RECOMBINANT PROTEIN, SYNTHETIC GENE AND USE OF SCULPTIN OR RECOMBINANT PROTEIN FOR PREPARING A MEDICAMENT OR PHARMACEUTICAL COMPOSITION FOR THE PROPHYLAXIS AND/OR TREATMENT OF THROMBOEMBOLIC DISEASES OR AS A DIRECT AND SPECIFIC INHIBITOR OF THROMBIN

(71) Applicant: Fundação Butantan, Butantã (BR)

(72) Inventors: Ana Marisa Chudzinski-Tavassi, Butantã (BR); Mauricio Barbugiani Goldfeder, Vila Mariana (BR); Asif Iqbal, Jardim Rizzo (BR)

(73) Assignee: Fundação Butantan, Butantã (BR)

( * ) Notice: Subject to any disclaimer, the term of this patent is extended or adjusted under 35 U.S.C. 154(b) by 1406 days.

(21) Appl. No.: 16/495,905

(22) PCT Filed: Mar. 21, 2018

(86) PCT No.: PCT/BR2018/050076
§ 371 (c)(1),
(2) Date: Sep. 20, 2019

(87) PCT Pub. No.: WO2018/170568
PCT Pub. Date: Sep. 27, 2018

(65) Prior Publication Data
US 2023/0151079 A1    May 18, 2023

(30) Foreign Application Priority Data
Mar. 21, 2017 (BR) .......................... 102017005783-6

(51) Int. Cl.
*C07K 14/81* (2006.01)
*A61K 38/00* (2006.01)

(52) U.S. Cl.
CPC ............ *C07K 14/811* (2013.01); *A61K 38/00* (2013.01)

(58) Field of Classification Search
CPC .............................. C07K 14/811; A61K 38/00
See application file for complete search history.

(56) References Cited

U.S. PATENT DOCUMENTS

| | | | | |
|---|---|---|---|---|
| 5,705,355 A | * | 1/1998 | Tolstoshev | C07K 14/815 530/324 |
| 5,767,235 A | * | 6/1998 | Nukui | C07K 14/815 530/328 |
| 5,919,762 A | * | 7/1999 | Schweden | A61P 7/02 530/324 |
| 6,034,060 A | | 3/2000 | Yamamoto et al. | |
| 6,156,540 A | | 12/2000 | Rosen et al. | |

FOREIGN PATENT DOCUMENTS

| | | | |
|---|---|---|---|
| CA | 2990065 A1 | 12/2016 | |
| CN | 1320165 A | 10/2001 | |
| CN | 1659180 A | 8/2005 | |
| CN | 1665526 A | 9/2005 | |
| CN | 101405017 A | 4/2009 | |
| CN | 102026652 A | 4/2011 | |
| CN | 103179982 A | 6/2013 | |
| CN | 107949569 A | 4/2018 | |
| EP | 1015491 A1 | 7/2000 | |
| WO | WO 90/03391 * | 4/1990 | ............... C07K 7/06 |
| WO | WO 00/56885 A1 | 9/2000 | |
| WO | WO 01/00667 A2 | 1/2001 | |
| WO | WO 01/42462 A2 | 6/2001 | |
| WO | WO 03/091284 A1 | 11/2003 | |
| WO | WO 2006/090282 A2 | 8/2006 | |
| WO | WO 2016/204696 A1 | 12/2016 | |

OTHER PUBLICATIONS

Martins et al., 2016, Geographical distribution of *Amblyomma cajennense* (sensu lato) ticks (Parasitiformes: Ixodidae) in Brazil, with description of the nymph of *A. canjennense* (sensu stricto), Parasites & Vectors, 9: 186 (14 pages).*
Asif, H. et al. The chloroplast genome sequence of *Syzygium cumini* (L.) and its relationship with other angiosperms. Tree Genet. Genomes 9, 867-877 (2013).
Batista, I. F. C. et al. Expressed sequence tags (ESTs) from the salivary glands of the tick *Amblyomma cajennense* (Acari: Ixodidae). Toxicon 51, 823-834 (2008).
Borensztajn, K. S. et al. Coagulation factor Xa drives tumor cells into apoptosis through BH3-only protein Bim up-regulation. Exp. Cell Res. 313, 2622-2633 (2007).
Borensztajn, K., Peppelenbosch, M. P. & Spek, C. A. Coagulation Factor Xa inhibits cancer cell migration via LIMK1-mediated cofilin inactivation. Thromb. Res. 125, e323-e328 (2010).
Borensztajn, K., Peppelenbosch, M. P. & Spek, C. A. Factor Xa: at the crossroads between coagulation and signaling in physiology and disease. Trends Mol. Med. 14, 429-440 (2008).
Branco, V. G. et al. Amblyomin-X having a Kunitz-type homologous domain, is a noncompetitive inhibitor of FXa and induces anticoagulation in vitro and in vivo. Biochim. Biophys. Acta BBA—Proteins Proteomics 1864, 1428-1435 (2016).
Coppens, M., Eikelboom, J. W., Gustafsson, D., Weitz, J. I. & Hirsh, J. Translational Success Stories: Development of Direct Thrombin Inhibitors. Circ. Res. 111, 920-929 (2012).

(Continued)

Primary Examiner — Amber D Steele
(74) Attorney, Agent, or Firm — Greenberg Traurig, LLP

(57) ABSTRACT

A class of proteins that inhibit thrombin, particularly direct inhibitor of thrombin modified from sculptin, identified in the transcriptomics analysis of the salivary glands of ticks, as well as fragments and recombinant protein thereof, which can be used as anticoagulant agents and for the prophylaxis and/or treatment of thromboembolic diseases. These proteins fall within the fields of biochemistry, molecular biology, genetics, pharmacy and medicinal chemistry, being related to biochemical and metabolic processes.

2 Claims, 10 Drawing Sheets
Specification includes a Sequence Listing.

(56) References Cited

OTHER PUBLICATIONS

Crawley, J. T. B., Zanardelli, S., Chion, C. K. N. K. & Lane, D. A. The central role of thrombin in hemostasis: Central role of thrombin in hemostasis. J. Thromb. Haemost. 5, 95-101 (2007).

Database UniProt [Online], Jun. 11, 2014 (Jun. 11, 2014), "SubName: Full=Putative tick hirudin 1 {ECO:0000313'EMBL: AC23844. 1};", XP55753468, retrieved from EBI accession No. Uniprot: A0A023FR72. Database accession No. A0A023FR72.

Database UniProt [Online] Jun. 11, 2014 (Jun. 11, 2014), "SubName: Full=Putative tick hirudin 3 {ECO:0000313} EMBL:AC24458.1}; Flags: Fragment;", XP55753459, retrieved from EBI accession No. Uniprot:A0A023FUV6 Database accession No. A0A023FUV6.

Database UniProt [Online] Oct. 14, 2015 (Oct. 14, 2015), "SubName: Full=Putative tick hirudin 1 {ECO:0000313}EMBL:AC24000. 1}; Flags: Fragment;", XP55753514, retrieved from EBI accession No. Uniprot: A0A023FTQ4. Database accession No. A0A023FTQ4.

Dodt, J., Köhler, S. & Baici, A. Interaction of site specific hirudin variants with α-thrombin. FEBS Lett. 229, 87-90 (1988).

Drozdetskiy, A., Cole, C., Procter, J. & Barton, G. J. JPred4: a protein secondary structure prediction server. Nucleic Acids Res. 43, W389-W394 (2015).

Francischetti, I. M. B., Valenzuela, J. G. & Ribeiro, J. M. C. Anophelin: Kinetics and Mechanism of Thrombin Inhibition. Biochemistry (Mosc.) 38, 16678-16685 (1999).

GenBank: BAD29729.1, "hirudin-like hypothetical protein [Amblyomma variegatum]", NCBI, pp. 1-4.

Gleeson, E. M. et al. Activated factor X signaling via protease-activated receptor 2 suppresses pro-inflammatory cytokine production from lipopolysaccharide-stimulated myeloid cells. Haematologica 99, 185-193 (2014).

Hsu, H.-J. et al. Factor Xa Active Site Substrate Specificity with Substrate Phage Display and Computational Molecular Modeling. J. Biol. Chem. 283, 12343-12353 (2008).

Iqbal, A. & Azim, M. K. Molecular characterization of hemolysin gene from a Pakistani clinical isolate of vibrio cholerae. J. Chem. Soc. Pak. 33, 935-938 (2011).

Iqbal, A. & Azim, M. K. Structural Bioinformatics of Enol Pyruvyl Shikimate Phosphate Synthase from Vibrio cholerae. J. Chem. Soc. Pak. 34, 120-126 (2012).

Iqbal, A., Azim, M. K., Hashmi, N., Ali, S. A. & Musharaf, S. G. Structural characterization of metalloprotease vibriolysin of cholera pathogen Vibrio cholerae. Protein Pept. Lett. 18, 287-294 (2011).

Iqbal et al: "Revisiting antithrombotic therapeutics; sculptin, a novel specific, competitive, reversible, scissile and tight binding inhibitor of thrombin", Scientific Reports, vol. 7, No. 1, May 3, 2017 (May 3, 2017), pp. 1-14, XP55608723, D0: 10.1038/s41598-017-01486-w.

Iqbal et al: "Supplementary data: Revisiting antithrombotic therapeutics; sculptin, a novel specific, competitive, reversible, scissile and tight binding inhibitor of thrombin", Scientific Reports, vol. 7, No. 1, Dec. 1, 2017 (Dec. 1, 2017), XP055756544, DOI: 10.1038/s41598-017-01486-w.

Kelly, L. M. FLT3 internal tandem duplication mutations associated with human acute myeloid leukemias induce myeloproliferative disease in a murine bone marrow transplant model. Blood 99, 310-318 (2002).

Kikumoto, R. et al. Selective inhibition of thrombin by (2R,4R)-4-methyl-1-[N2-[1,2,3,4- tetrahydro-8-quinolinyl)sulfonyl]-L-arginyl]-2-piperidinecarboxylic acid. Biochemistry (Mosc.) 23, 85-90 (1984).

Kumar, S., Stecher, G. & Tamura, K. MEGA7: Molecular Evolutionary Genetics Analysis Version 7.0 for Bigger Datasets. Mol. Biol. Evol. 33, 1870-1874 (2016).

Lee, C. J. & Ansell, J. E. Direct thrombin inhibitors: Parenteral and oral inhibitors of thrombin activity. Br. J. Clin. Pharmacol. 72, 581-592 (2011).

Liao, M. et al. Hemalin, a thrombin inhibitor isolated from a midgut cDNA library from the hard tick *Haemaphysalis longicornis*. J. Insect Physiol. 55, 165-174 (2009).

Macedo-Ribeiro, S. et al. Isolation, Cloning and Structural Characterisation of Boophilin, a Multifunctional Kunitz-Type Proteinase Inhibitor from the Cattle Tick. PLoS One 3, e1624 (2008).

Maraganore, J. M., Bourdon, P., Jablonski, J., Ramachandran, K. L. & Fenton, J. W. Design and characterization of hirulogs: a novel class of bivalent peptide inhibitors of thrombin. Biochemistry (Mosc.) 29, 7095-7101 (1990).

Martins-Pinheiro, M., Lima, W. C., Asif, H., Oller, C. A. & Menck, C. F. M. Evolutionary and Functional Relationships of the dha Regulon by Genomic Context Analysis. PLOS One 11, e0150772 (2016).

Narasimhan, S. et al. Characterization of Ixophilin, A Thrombin Inhibitor from the Gut of Ixodes scapularis. PLoS One 8, e68012 (2013).

Nasief, N. N., Said, A. M. & Hangauer, D. Modulating hydrogen-bond basicity within the context of protein-ligand binding: A case study with thrombin inhibitors that reveals a dominating role for desolvation. Eur. J. Med. Chem. 125, 975-991 (2017).

Nava, S. et al. Reassessment of the taxonomic status of Amblyomma cajennense () with the description of three new species, *Amblyomma tonelliae* n. sp., *Amblyomma interandinum* n. sp. and *Amblyomma patinoi* n. sp., and reinstatement of Amblyomma mixtum, and Amblyomma sculptum (Ixodida: Ixodidae). Ticks Tick-Borne Dis. 5, 252-276 (2014).

Parry, M. A. A., Maraganore, J. M. & Stone, S. R. Kinetic Mechanism for the Interaction of Hirulog with Thrombin. Biochemistry (Mosc.) 33, 14807-14814 (1994).

Posma, J. J. N., Posthuma, J. J. & Spronk, H. M. H. Coagulation and non-coagulation effects of thrombin. J. Thromb. Haemost. 14, 1908-1916 (2016).

Šali, A. & Blundell, T. L. Comparative Protein Modelling by Satisfaction of Spatial Restraints. J. Mol. Biol. 234, 779-815 (1993).

Sierko, E. et al. Co-localization of Protein Z, Protein Z-Dependent protease inhibitor and coagulation factor X in human colon cancer tissue: Implications for coagulation regulation on tumor cells. Thromb. Res. 129, e112-e118 (2012).

Siller-Matula, J. M., Schwameis, M., Blann, A., Mannhalter, C. & Jilma, B. Thrombin as a multi-functional enzyme: Focus on in vitro and in vivo effects. Thromb. Haemost. 106, 1020-1033 (2011).

Song, X. et al. The NMR solution structure of recombinant RGD-hirudin. Biochem. Biophys. Res. Commun. 360, 103-108 (2007).

Stone, S. R. & Hofsteenge, J. Kinetics of the inhibition of thrombin by hirudin. Biochemistry (Mosc.) 25, 4622-4628 (1986).

Tan, S. et al. Efficient expression and secretion of recombinant hirudin III in *E. coli* using the 1-asparaginase II signal sequence. Protein Expr. Purif. 25, 430-436 (2002).

Tao, C., Jin, X., Zhu, L. & Li, H. Two-Dimensional Gel Electrophoresis-Based Proteomic Analysis Reveals N-terminal Truncation of the Hsc70 Protein in Cotton Fibers In vivo. Sci. Rep. 6, 36961 (2016).

Tew, D. J. & Bottomley, S. P. Intrinsic fluorescence changes and rapid kinetics of proteinase deformation during serpin inhibition. FEBS Lett. 494, 30-33 (2001).

Tulinsky, A. Molecular Interactions of Thrombin. Semin. Thromb. Hemost. 22, 117-124 (1996).

Usón, I. et al. The 1.2 Å crystal structure of hirustasin reveals the intrinsic flexibility of a family of highly disulphide-bridged inhibitors. Structure 7, 55-63 (1999).

Weitz, J. I., Hudoba, M., Massel, D., Maraganore, J. & Hirsh, J. Clot-bound thrombin is protected from inhibition by heparin-antithrombin III but is susceptible to inactivation by antithrombin III-independent inhibitors. J. Clin. Invest. 86, 385-391 (1990).

Weitz, J. I., Leslie, B. & Hudoba, M. Thrombin Binds to Soluble Fibrin Degradation Products Where it is Protected From Inhibition by Heparin-Antithrombin but Susceptible to Inactivation by Antithrombin-Independent Inhibitors. Circulation 97, 544-552 (1998).

Witting, J. I., Bourdon, P., Brezniak, D. V., Maraganore, J. M. & Fenton, J. W. Thrombin-specific inhibition by and slow cleavage of hirulog-1. Biochem. J. 283, 737-743 (1992).

Zavyalova, E. & Kopylov, A. Multiple inhibitory kinetics reveal an allosteric interplay among thrombin functional sites. Thromb. Res. 135, 212-216 (2015).

(56) References Cited

OTHER PUBLICATIONS

Zhang X, Lyu SH, Wang JH. Progress in the study of anticoagulant substances from ticks[J]. Chin J Cell Biol, 2016, 38(12): 1572-1578. DOI : 10.11844/cjcb.2016.12.0123.

* cited by examiner

SEQUENCE LISTING

<160> NUMBER OF SEQ ID NOS: 26

<210> SEQ ID NO 1
<211> LENGTH: 157
<212> TYPE: PRT
<213> ORGANISM: Artificial Sequence
<220> FEATURE:
<223> OTHER INFORMATION: Description of Artificial Sequence: Synthetic

```
                        polypeptide
<220> FEATURE:
<223> OTHER INFORMATION: Sculptin recombinat protein

<400> SEQUENCE: 1

Gly Lys Pro Gln Gly His Pro His Asp Ala Leu Glu Ala Arg Ser Asp
1               5                   10                  15

Ala Val His Thr Ala Val Pro Lys Met Pro Lys Gly Gly His Gly Gly
            20                  25                  30

Phe Glu Pro Ile Pro Ile Asp Tyr Asp Glu Arg Ala Leu Glu Ala Arg
        35                  40                  45

Ser Asp Ala Val His Thr Ala Val Pro Lys Met Pro Lys Gly Gly Leu
50                  55                  60

Gly Gly Phe Glu Pro Ile Pro Ile Asp Tyr Asp Glu Arg Ala Leu Glu
65                  70                  75                  80

Ala Arg Ser Asp Ala Val His Thr Ala Val Pro Lys Met Pro Lys Gly
                85                  90                  95

Gly His Gly Gly Phe Glu Pro Ile Pro Ile Asp Tyr Asp Glu Arg Ala
            100                 105                 110

Leu Glu Ala Arg Ser Asp Ala Val His Thr Ala Val Pro Lys Met Pro
        115                 120                 125

Lys Gly Gly His Gly Gly Phe Glu Pro Ile Pro Ile Asp Tyr Asp Glu
    130                 135                 140

Arg Ala Leu His Ala Leu Glu His His His His His
145                 150                 155

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sculptin fragments generated by thrombin

<400> SEQUENCE: 2

Gly Lys Pro Gln Gly His Pro His Asp Ala Leu Glu Ala Arg Ser Asp
1               5                   10                  15

Ala Val His Thr Ala Val Pro Lys
            20

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 3

Gly Lys Pro Gln Gly His Pro His Asp Ala Leu Glu Ala Arg Ser Asp
1               5                   10                  15

Ala Val His Thr Ala Val Pro Lys Met Pro Lys Gly Gly His Gly Gly
            20                  25                  30

Phe Glu Pro Ile Pro Ile Asp Tyr Asp Glu Arg Ala Leu Glu Ala Arg
        35                  40                  45

Ser Asp Ala Val His Thr Ala Val Pro Lys
50                  55
```

```
<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 4

Met Pro Lys Gly Gly His Gly Gly Phe Glu Pro Ile Pro Ile Asp Tyr
1               5                   10                  15

Asp Glu Arg Ala Leu Glu Ala Arg Ser Asp Ala Val His Thr Ala Val
            20                  25                  30

Pro Lys

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 5

Met Pro Lys Gly Gly His Gly Gly Phe Glu Pro Ile Pro Ile Asp Tyr
1               5                   10                  15

Asp Glu Arg Ala Leu His Ala Leu Glu His His His His His
            20                  25                  30

<210> SEQ ID NO 6
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 6

Met Pro Lys Gly Gly His Gly Gly Phe Glu Pro Ile Pro Ile Asp Tyr
1               5                   10                  15

Asp Glu Arg Ala Leu Glu Ala Arg Ser Asp Ala Val His Thr Ala Val
            20                  25                  30

Pro Lys Met Pro Lys Gly Gly His Gly Gly Phe Glu Pro Ile Pro Ile
        35                  40                  45

Asp Tyr Asp Glu Arg Ala Leu His Ala Leu Glu His His His His
    50                  55                  60

His
65

<210> SEQ ID NO 7
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin
```

```
<400> SEQUENCE: 7

Met Pro Lys Gly Gly His Gly Gly Phe Glu Pro Ile Pro Ile Asp Tyr
1               5                   10                  15

Asp Glu Arg Ala Leu Glu Ala Arg Ser Asp Ala Val His Thr Ala Val
            20                  25                  30

Pro Lys Met Pro Lys Gly Gly Leu Gly Gly Phe Glu Pro Ile Pro Ile
        35                  40                  45

Asp Tyr Asp Glu Arg Ala Leu Glu Ala Arg Ser Asp Ala Val His Thr
    50                  55                  60

Ala Val Pro Lys
65

<210> SEQ ID NO 8
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 8

Met Pro Lys Gly Gly Leu Gly Gly Phe Glu Pro Ile Pro Ile Asp Tyr
1               5                   10                  15

Asp Glu Arg Ala Leu Glu Ala Arg Ser Asp Ala Val His Thr Ala Val
            20                  25                  30

Pro Lys Met Pro Lys Gly Gly His Gly Gly Phe Glu Pro Ile Pro Ile
        35                  40                  45

Asp Tyr Asp Glu Arg Ala Leu Glu Ala Arg Ser Asp Ala Val His Thr
    50                  55                  60

Ala Val Pro Lys Met Pro Lys Gly Gly His Gly Gly Phe Glu Pro Ile
65                  70                  75                  80

Pro Ile Asp Tyr Asp Glu Arg Ala Leu His Ala Leu Glu His His His
                85                  90                  95

His His His

<210> SEQ ID NO 9
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by thrombin

<400> SEQUENCE: 9

Met Pro Lys Gly Gly His Gly Gly Phe Glu Pro Ile Pro Ile Asp Tyr
1               5                   10                  15

Asp Glu Arg Ala Leu Glu Ala Arg Ser Asp Ala Val His Thr Ala Val
            20                  25                  30

Pro Lys Met Pro Lys Gly Gly Leu Gly Gly Phe Glu Pro Ile Pro Ile
        35                  40                  45

Asp Tyr Asp Glu Arg Ala Leu Glu Ala Arg Ser Asp Ala Val His Thr
    50                  55                  60

Ala Val Pro Lys Met Pro Lys Gly Gly His Gly Gly Phe Glu Pro Ile
65                  70                  75                  80
```

```
Pro Ile Asp Tyr Asp Glu Arg Ala Leu Glu Ala Arg Ser Asp Ala Val
            85                  90                  95

His Thr Ala Val Pro Lys Met Pro Lys Gly Gly His Gly Gly Phe Glu
            100                 105                 110

Pro Ile Pro Ile Asp Tyr Asp Glu Arg Ala Leu His Ala Leu Glu His
        115                 120                 125

His His His His His
        130

<210> SEQ ID NO 10
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 10

Gly Lys Pro Gln Gly His Pro His Asp Ala Leu Glu Ala Arg Ser Asp
1               5                   10                  15

Ala Val His Thr Ala Val Pro Lys Met Pro Lys Gly Gly His Gly Gly
            20                  25                  30

Phe Glu Pro Ile Pro Ile Asp Tyr Asp Glu Arg Ala Leu Glu Ala Arg
        35                  40                  45

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 11

Ser Asp Ala Val His Thr Ala Val Pro Lys Met Pro Lys Gly Gly His
1               5                   10                  15

Gly Gly Phe Glu Pro Ile Pro Ile Asp Tyr Asp Glu Arg Ala Leu Glu
            20                  25                  30

Ala Arg

<210> SEQ ID NO 12
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 12

Ser Asp Ala Val His Thr Ala Val Pro Lys Met Pro Lys Gly Gly His
1               5                   10                  15

Gly Gly Phe Glu Pro Ile Pro Ile Asp Tyr Asp Glu Arg Ala Leu His
            20                  25                  30

Ala Leu Glu His His His His His His
        35                  40

<210> SEQ ID NO 13
```

```
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 13

Ser Asp Ala Val His Thr Ala Val Pro Lys Met Pro Lys Gly Gly His
1               5                   10                  15

Gly Gly Phe Glu Pro Ile Pro Ile Asp Tyr Asp Glu Arg Ala Leu Glu
            20                  25                  30

Ala Arg Ser Asp Ala Val His Thr Ala Val Pro Lys Met Pro Lys Gly
        35                  40                  45

Gly His Gly Gly Phe Glu Pro Ile Pro Ile Asp Tyr Asp Glu Arg Ala
    50                  55                  60

Leu His Ala Leu Glu His His His His His
65                  70                  75

<210> SEQ ID NO 14
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 14

Ser Asp Ala Val His Thr Ala Val Pro Lys Met Pro Lys Gly Gly His
1               5                   10                  15

Gly Gly Phe Glu Pro Ile Pro Ile Asp Tyr Asp Glu Arg Ala Leu Glu
            20                  25                  30

Ala Arg Ser Asp Ala Val His Thr Ala Val Pro Lys Met Pro Lys Gly
        35                  40                  45

Gly His Gly Gly Phe Glu Pro Ile Pro Ile Asp Tyr Asp Glu Arg
    50                  55                  60

<210> SEQ ID NO 15
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 15

Ser Asp Ala Val His Thr Ala Val Pro Lys Met Pro Lys Gly Gly His
1               5                   10                  15

Gly Gly Phe Glu Pro Ile Pro Ile Asp Tyr Asp Glu Arg Ala Leu Glu
            20                  25                  30

Ala Arg Ser Asp Ala Val His Thr Ala Val Pro Lys Met Pro Lys Gly
        35                  40                  45

Gly His Gly Gly Phe Glu Pro Ile Pro Ile Asp Tyr Asp Glu Arg Ala
    50                  55                  60

Leu Glu Ala Arg
65
```

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Sculptin fragments generated by Xa factor

<400> SEQUENCE: 16

Gly Lys Pro Gln Gly His Pro His Asp Ala Leu Glu Ala Arg Ser Asp
1               5                   10                  15

Ala Val His Thr Ala Val Pro Lys Met Pro Lys Gly Gly His Gly Gly
            20                  25                  30

Phe Glu Pro Ile Pro Ile Asp Tyr Asp Glu Arg Ala Leu Glu Ala Arg
        35                  40                  45

Ser Asp Ala Val His Thr Ala Val Pro Lys Met Pro Lys Gly Gly Leu
    50                  55                  60

Gly Gly Phe Glu Pro Ile Pro Ile Asp Tyr Asp Glu Arg Ala Leu Glu
65              70                  75                  80

Ala Arg Ser Asp Ala Val His Thr Ala Val Pro Lys Met Pro Lys Gly
                85                  90                  95

Gly His Gly Gly Phe Glu Pro Ile Pro Ile Asp Tyr Asp Glu Arg Ala
            100                 105                 110

Leu Glu Ala Arg
        115

<210> SEQ ID NO 17
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Synthetic gene encoding sculptin

<400> SEQUENCE: 17
atgggtaagc tcaagggca tccacacgac gcactggagg cccgtagcga cgcagtgcat      60
accgctgtcc ctaagatgcc gaagggcggc acggtgggt ttgaaccgat ccgattgat     120 tatgacgaac gcgcactgga agctcgcagt gacgcggtac atactgctgt gcctaaaatg    180
ccaaaagggg gcctgggggg tttcgagccg atcccgattg attatgacga gcgcgcactg    240
gaagctcgta gcgacgcagt acatactgct gtaccaaaaa tgcctaaagg gggtcacggg    300
gggtttgaac cgattccgat cgattacgac gaacgtgcgc tggaagcgcg ttctgatgcc    360
gtccatacgg cggtgccaaa aatgcctaaa ggcggtcatg gtggcttcga acctattcca    420
atcgattacg acgaacgtgc cctgcacgca ctcgagcacc accaccacca ccactga       477

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Lys Pro Gln Gly
1               5

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Pro Lys Gly Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Asp Ala Val His
1               5

<210> SEQ ID NO 21
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Lys Asn Ile Ile Val Leu Leu Ala Val Ala Leu Thr Gly Pro
1               5                   10                  15

Ala Val Leu Ala Lys Pro Gln Gly His Pro His Asp Ala Leu Glu Ala
                20                  25                  30

Arg Ser Asp Ala Val His Thr Ala Val Pro Lys Met Pro Lys Gly Gly
            35                  40                  45

His Gly Gly Phe Glu Pro Ile Pro Ile Asp Tyr Asp Glu Arg Ala Leu
        50                  55                  60

Glu Ala Arg Ser Asp Ala Val His Thr Ala Val Pro Lys Met Pro Lys
65                  70                  75                  80

Gly Gly Leu Gly Gly Phe Glu Pro Ile Pro Ile Asp Tyr Asp Glu Arg
                85                  90                  95

Ala Leu Glu Ala Arg Ser Asp Ala Val His Thr Ala Val Pro Lys Met
                100                 105                 110

Pro Lys Gly Gly His Gly Gly Phe Glu Pro Ile Pro Ile Asp Tyr Asp
            115                 120                 125

Glu Arg Ala Leu Glu Ala Arg Ser Asp Ala Val His Thr Ala Val Pro
        130                 135                 140

Lys Met Pro Lys Gly Gly His Gly Gly Phe Glu Pro Ile Pro Ile Asp
145                 150                 155                 160

Tyr Asp Glu Arg Ala Leu His Ala
                165

<210> SEQ ID NO 22
<211> LENGTH: 42
<212> TYPE: PRT
<213> ORGANISM: Amblyomma cajennense
```

```
<400> SEQUENCE: 22

Lys Pro Arg Gly Tyr Pro His Asp Ala Leu Glu Ala Arg Ser Asp Ala
1               5                   10                  15

Val His Thr Ala Val Pro Lys Met Pro Lys Gly Gly His Gly Gly Phe
            20                  25                  30

Glu Pro Ile Pro Ile Asp Tyr Glu Arg
        35                  40

<210> SEQ ID NO 23
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Lys Pro Gln Gly His Pro His Asp Ala Leu Glu Ala Arg Ser Asp
1               5                   10                  15

Ala Val His Thr Ala Val Pro Lys Met Pro Lys Gly Gly His Gly Gly
            20                  25                  30

Phe Glu Pro Ile Pro Ile Asp Tyr Asp Glu Arg
        35                  40

<210> SEQ ID NO 24
<211> LENGTH: 70
<212> TYPE: PRT
<213> ORGANISM: Rhipicephalus appendiculatus

<400> SEQUENCE: 24

Met Pro Arg Gln Asn Leu Arg Gln Arg Lys Leu Ser Asn Asp Leu Glu
1               5                   10                  15

Ala Arg Ala Ala Val Ala Ser Thr Asp Tyr Glu Ser Asp Glu Asp Ser
            20                  25                  30

Val Gly Gly Gly Ser Lys Gly Ser Ala Val Ala Arg Pro Lys Ala Lys
        35                  40                  45

Arg Asp Asn Ser Gly Ser Gly Asp Phe Glu Ser Ile Pro Ile Pro Gly
    50                  55                  60

Met Arg Asp Ser Gln Ala
65                  70

<210> SEQ ID NO 25
<211> LENGTH: 65
<212> TYPE: PRT
<213> ORGANISM: Hirudo medicinalis

<400> SEQUENCE: 25

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 26
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His His His His His His
1               5
```

RECOMBINANT PROTEIN AND FRAGMENTS THEREOF, METHOD FOR PRODUCING SAID RECOMBINANT PROTEIN, SYNTHETIC GENE AND USE OF SCULPTIN OR RECOMBINANT PROTEIN FOR PREPARING A MEDICAMENT OR PHARMACEUTICAL COMPOSITION FOR THE PROPHYLAXIS AND/OR TREATMENT OF THROMBOEMBOLIC DISEASES OR AS A DIRECT AND SPECIFIC INHIBITOR OF THROMBIN

SEQUENCE LISTING

The instant application contains a Sequence Listing which has been submitted electronically in ASCII format and is hereby incorporated by reference in its entirety. Said ASCII copy, created on Nov. 22, 2023, is named 218550-010100_SL.txt and is 18,939 bytes in size.

FIELD OF THE INVENTION

The present invention describes a new class of inhibitor proteins of thrombin, particularly direct inhibitors of thrombin, as well as fragments and recombinant protein thereof which can be used as anticoagulant agents. The present invention is within the fields of biochemistry, molecular biology, genetics, pharmacy, medicinal chemistry, being related to Biochemical and Metabolic processes.

BACKGROUND OF THE INVENTION

Thrombin is a multifunctional enzyme with main function in the coagulation cascade. Its functional modulation may result in normal blood coagulation or in disorders, such as thrombosis. Therefore, the identification of novel strong and specific inhibitors of thrombin is of great importance.

Blood coagulation is a dynamic process involving a pro-enzymes cascade leading to a downstream activation of enzymes. In normal conditions, it results in homeostasis. Thrombo-hemorrhagic balance is crucially maintained in the body through a complex and contentious mechanism. However, the disorder thereof may likely result in hemorrhage or thrombosis. Thrombin, a 37 kDa heterodimer, is a central enzyme in the coagulation cascade. Thrombin is a multi-function enzyme acting as a procoagulant through fibrinogen cleavage, which activates coagulation factors (V, VIII, XI, and XIII) and induces platelet aggregation. By the other hand, thrombin may act as an anticoagulant through thrombomodulin binding and activates protein C. In addition, it plays a vital role in arterial and venous thrombosis, disseminated intravascular coagulation (DIC), cancer, inflammatory brain diseases, wound healing and atherosclerosis. In order to overcome its harmful effects, thrombin may be inhibited directly or indirectly by blockage of one or two of its three domains, i.e., active site and exosite 1 and 2. Traditionally, unfractionated heparin (UFH) and low molecular weight heparin (LMWH) have been used as anticoagulants for inhibiting thrombin indirectly by linking simultaneously to anti-thrombin and exosite 2 of thrombin. However, heparin (UFH and LMWH) yields a fibrin-thrombin bridge and increases thrombus formation, and may cause heparin-induced thrombocytopenia. Direct thrombin inhibitors (DTIs) are a group of anticoagulants not requiring a co-factor, which are directly bound to active site of thrombin and block its activity. DTIs have an advantage over indirect inhibitors, because DTIs are more predictable anticoagulants, since they have not antiplatelet effect and they do not result in immune-mediated thrombocytopenia. Several DTIs, including recombinant hirudin and hirulogs thereof, are approved for use as anticoagulants. Hirudin, a 65 amino acid peptide (7 kDa), is a direct thrombin inhibitor which was, firstly, isolated from saliva of medicinal leech *Hirudo medicinalis*. Next, a recombinant hirudin form was produced, differing from native hirudin due to the Tyr residue, which is not sulfated. Such difference slightly decreased the recombinant hirudin activity. However, thrombin inhibition through recombinant hirudin is irreversible and generates anti-hirudin antibodies, resulting in drug accumulation. Currently, there is no antidote for reversing recombinant hirudin consequences. In addition, several synthetic hirulogs were developed and tested regarding its inhibitor activity for thrombin, but these inhibitors were almost 800 timer weaker than recombinant hirudin. Among all hirulogs, bivalirudin is a FDA-approved anticoagulant, being a direct thrombin-inhibitor, but presenting short half-life. Almost all of such anticoagulants are related to side effects, like irreversible formation of hirudin-thrombin complex, short half-life of hirulogs, and their dosage should be closely monitored. The most of such thrombin inhibitors are from leeches and are extensively investigated. On the other hand, thrombin-specific inhibitors from ticks were totally forgotten, though Kunitz-type inhibitors had been investigated in detail.

Due to those facts, it is interesting the development of a novel class of direct thrombin inhibitors, as well as fragments thereof and recombinant protein, which can be used as anticoagulant agents.

In search of the state of the art in scientific and patent literature, the following documents approaching this theme were found:

1. Posma, J. J. N., Posthuma, J. J. & Spronk, H. M. H. Coagulation and non-coagulation effects of thrombin. *J. Thromb. Haemost.* 14, 1908-1916 (2016).
2. Lee, C. J. & Ansell, J. AND. Direct thrombin inhibitors: Parenteral and oral inhibitors of thrombin activity. *Br. J. Clin. Pharmacol.* 72, 581-592 (2011).
3. Crawley, J. T. B., Zanardelli, S., Chion, C. K. N. K. & Lane, D. A. The central role of thrombin in hemostasis: Central role of thrombin in hemostasis. *J. Thromb. Haemost.* 5, 95-101 (2007).
4. Siller-Matula, J. M., Schwameis, M., Blann, A., Mannhalter, C. & Jilma, B. Thrombin as a multi-functional enzyme: Focus on in vitro and in vivo effects. *Thromb. Haemost.* 106, 1020-1033 (2011).
5. Coppens, M., Eikelboom, J. W., Gustafsson, D., Weitz, J. I. & Hirsh, J. Translational Success Stories: Development of Direct Thrombin Inhibitors. *Circ. Res.* 111, 920-929 (2012).
6. Weitz, J. I., Hudoba, M., Massel, D., Maraganore, J. & Hirsh, J. Clot-bound thrombin is protected from inhibition by heparin-antithrombin III but is susceptible to inactivation by antithrombin III-independent inhibitors. *J. Clin. Invest.* 86, 385-391 (1990).
7. Nasief, N. N., Said, A. M. & Hangauer, D. Modulating hydrogen-bond basicity within the context of protein-ligand binding: A case study with thrombin inhibitors that reveals a dominating role for desolvation. *Eur. J. Med. Chem.* 125, 975-991 (2017).
8. Song, X. et al. The NMR solution structure of recombinant RGD-hirudin. *Biochem. Biophys. Res. Commun.* 360, 103-108 (2007).
9. Tulinsky, A. Molecular Interactions of Thrombin. *Semin. Thromb. Hemost.* 22, 117-124 (1996).

10. Weitz, J. I., Leslie, B. & Hudoba, M. Thrombin Binds to Soluble Fibrin Degradation Products Where it Is Protected From Inhibition by Heparin-Antithrombin but Susceptible to Inactivation by Antithrombin-Independent Inhibitors. *Circulation* 97, 544-552 (1998).
11. Dodt, J., Köhler, S. & Baici, A. Interaction of site specific hirudin variants with α-thrombin. *FEBS Lett.* 229, 87-90 (1988).
12. Zavyalova, AND. & Kopylov, A. Multiple inhibitory kinetics reveal an allosteric interplay among thrombin functional sites. *Thromb. Res.* 135, 212-216 (2015).
13. Maraganore, J. M., Bourdon, P., Jablonski, J., Ramachandran, K. L. & Fenton, J. W. Design and characterization of hirulogs: a novel class of bivalent peptide inhibitors of thrombin. *Biochemistry (Mosc.)* 29, 7095-7101 (1990).
14. Branco, V. G. et al. Amblyomin-X having a Kunitz-type homologous domain, is a noncompeting inhibitor of FXa and induces anticoagulation in vitro and in vivo. *Biochim. Biophys. Acta BBA-Proteins Proteomics* 1864, 1428-1435 (2016).
15. Macedo-Ribeiro, S. et al. Isolation, Cloning and Structural Characterisation of Boophilin, a Multifunctional Kunitz-Type Proteinase Inhibitor from the Cattle Tick. *PLOS ONE* 3, e1624 (2008).
16. Narasimhan, S. et al. Characterization of Ixophilin, A Thrombin Inhibitor from the Gut of *Ixodes scapularisl. PLOS ONE* 8, e68012 (2013).
17. Liao, M. et al. Hemalin, a thrombin inhibitor isolated from a midgut cDNA library from the hard tick *Haemaphysalis longicornis. J. Insect Physiol.* 55, 165-174 (2009).
18. Nava, S. et al. Reassessment of the taxonomic status of *Amblyomma* cajennense ( ) with the description of three new species, *Amblyomma* tonelliae n. sp., *Amblyomma interandinum* n. sp. and *Amblyomma patinoi* n. sp., and reinstatement of *Amblyomma mixtum*, and *Amblyomma* sculptum (Ixodida: Ixodidae). *Ticks Tick-Borne Dis.* 5, 252-276 (2014).
19. Batista, I. F. C. et al. Expressed sequence tags (ESTs) from the salivary glands of the tick *Amblyomma cajennense* (Acari: Ixodidae). *Toxicon* 51, 823-834 (2008).
20. Kelly, L. M. FLT3 internal tandem duplication mutations associated with human acute myeloid leukemias induce myeloproliferative disease in a murine bone marrow transplant model. *Blood* 99, 310-318 (2002).
21. Usón, I. et al. The 1.2 Å crystal structure of hirustasin reveals the intrinsic flexibility of a family of highly disulphide-bridged inhibitors. *Structure* 7, 55-63 (1999).
22. Tan, S. et al. Efficient expression and secretion of recombinant hirudin III in AND. coli using the I-asparaginase II signal sequence. *Protein Expr. Purif.* 25, 430-436 (2002).
23. Kikumoto, R. et al. Selective inhibition of thrombin by (2R,4R)-4-methyl-1-[N2-[1,2,3,4-tetrahydro-8-quinolinyl) sulfonyl]-L-arginyl]-2-piperidinecarboxylic acid. *Biochemistry (Mosc.)* 23, 85-90 (1984).
24. Tew, D. J. & Bottomley, S. P. Intrinsic fluorescence changes and rapid kinetics of proteinase deformation during serpin inhibition. *FEBS Lett.* 494, 30-33 (2001).
25. Witting, J. I., Bourdon, P., Brezniak, D. V., Maraganore, J. M. & Fenton, J. W. Thrombin-specific inhibition by and slow cleavage of hirulog-1. *Biochem. J.* 283, 737-743 (1992).
26. Parry, M. A. A., Maraganore, J. M. & Stone, S. R. Kinetic Mechanism for the Interaction of Hirulog with Thrombin. *Biochemistry (Mosc.)* 33, 14807-14814 (1994).
27. Hsu, H.-J. et al. Factor Xa Active Site Substrate Specificity with Substrate Phage Display and Computational Molecular Modeling. *J. Biol. Chem.* 283, 12343-12353 (2008).
28. Borensztajn, K., Peppelenbosch, M. P. & Spek, C. A. Factor Xa: at the crossroads between coagulation and signaling in physiology and disease. *Trends Mol. Med.* 14, 429-440 (2008).
29. Borensztajn, K. S. et al. Coagulation factor Xa drives tumor cells into apoptosis through BH3-only protein Bim up-regulation. *Exp. Cell Res.* 313, 2622-2633 (2007).
30. Borensztajn, K., Peppelenbosch, M. P. & Spek, C. A. Coagulation Factor Xa inhibits cancer cell migration via LIMK1-mediated cofilin inactivation. *Thromb. Res.* 125, e323-e328 (2010).
31. Gleeson, AND. M. et al. Activated factor X signaling via protease-activated receptor 2 suppresses pro-inflammatory cytokine production from lipopolysaccharide-stimulated myeloid cells. *Haematologica* 99, 185-193 (2014).
32. Sierko, A N D. et al. Co-localization of Protein Z, Protein Z-Dependent protease inhibitor and coagulation factor X in human colon cancer tissue: Implications for coagulation regulation on tumor cells. *Thromb. Res.* 129, e112-e118 (2012).
33. Drozdetskiy, A., Cole, C., Procter, J. & Barton, G. J. JPred4: a protein secondary structure prediction server. *Nucleic Acids Res.* 43, W389-W394 (2015).
34. Kumar, S., Stecher, G. & Tamura, K. MEGA7: Molecular Evolutionary Genetics Analysis Version 7.0 for Bigger Datasets. *Mol. Biol. Evol.* 33, 1870-1874 (2016).
35. Asif, H. et al. The chloroplast genome sequence of Syzygium cumini (L.) and its relationship with other angiosperms. *Tree Genet. Genomes* 9, 867-877 (2013).
36. Iqbal, A. & Azim, M. K. Molecular characterization of hemolysin gene from a Pakistani clinical isolate of *Vibrio cholerae. J. Chem. Soc. Pak.* 33, 935-938 (2011).
37. Martins-Pinheiro, M., Lima, W. C., Asif, H., Oller, C. A. & Menck, C. F. M. Evolutionary and Functional Relationships of the dha Regulon by Genomic Context Analysis. *PLOS ONE* 11, e0150772 (2016).
38. Francischetti, I. M. B., Valenzuela, J. G. & Ribeiro, J. M. C. Anophelin: Kinetics and Mechanism of Thrombin Inhibition. *Biochemistry (Mosc.)* 38, 16678-16685 (1999).
39. Iqbal, A., Azim, M. K., Hashmi, N., Ali, S. A. & Musharaf, S. G. Structural characterization of metalloprotease vibriolysin of cholera pathogen *Vibrio cholerae. Protein Pept. Lett.* 18, 287-294 (2011).
40. Šali, A. & Blundell, T. L. Comparative Protein Modelling by Satisfaction of Spatial Restraints. *J. Mol. Biol.* 234, 779-815 (1993).
41. Iqbal, A. & Azim, M. K. Structural Bioinformatics of Enol Pyruvyl Shikimate Phosphate Synthase from *Vibrio cholerae. J. Chem. Soc. Pak.* 34, 120-126 (2012).
42. Tao, C., Jin, X., Zhu, L. & Li, H. Two-Dimensional Gel Electrophoresis-Based Proteomic Analysis Reveals N-terminal Truncation of the Hsc70 Protein in Cotton Fibers *In vivo. Sci. Rep.* 6, 36961 (2016).
43. Stone, S. R. & Hofsteenge, J. Kinetics of the inhibition of thrombin by hirudin. *Biochemistry (Mosc.)* 25, 4622-4628 (1986).

Therefore, from what is inferred from the searched literature, there are no documents antecipating or suggesting the teachings from the present invention, such that the solution proposed herein has novelty and inventive activity against the state of the art.

The solution proposed herein solves the problem of absence of alternative ways to overcome the limitations from antithrombotic therapies or for the treatment or prophylaxis of thromboembolic diseases.

SUMMARY OF THE INVENTION

Therefore, the present invention has the object to solve the problems present in the state of the art as from the development of novel proteins with antithrombotic proprieties or for the treatment or prophylaxis of thromboembolic diseases and/or fragments thereof, acting in direct and specific inhibition of thrombin.

Nucleotide sequence used in expression vector is not the same as the sequence naturally found. Amino acid sequence has been identified by analyzing the library of cDNA of tick salivary gland, however codon optimization, addition of restriction sites and histidine tail were performed for purifying the nucleotide sequence used in expression vector, which enabled the development of the process for obtaining the recombinant protein (modification of sculptin originally present in tick salivary gland) on a large scale, using bacteria E. coli, and exclusively such recombinant protein was used in all studies.

Such obtained molecule inhibited selectively thrombin in a competing way. It was slowly cleaved by thrombin and factor Xa. Based on mass spectrometry and Edman analysis, the binding peptide of thrombin active site was proposed, having only few conserved residues compared to classic hirudin from medicinal leech, but it presents the same strength. Gathered data led to conclude that such molecule has the potential to become an anti-thrombotic drug and may potentially compete with classic hirudin and analogues thereof.

The present invention has the first object a recombinant protein comprising one sequence with at least 60% of identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same. Being SEQ ID NO: 1 related to recombinant protein, while SEQ ID NO: 2 to 16 are related to fragments thereof. In one embodiment, recombinant protein comprises one sequence with SEQ ID NO: 1 or SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same.

The present invention has the second object of a process for obtaining said recombinant protein and/or fragments thereof from salivary gland cDNA from the tick *Amblyoma cajennense*.

The present invention has the third object of a synthetic gene comprising one sequence with at least 60% of identity with SEQ ID NO: 17. In one embodiment, synthetic gene comprises one sequence with SEQ ID NO: 17.

In a fourth object, the present invention presents the use of sculptin or recombinant protein for preparing a medication or pharmaceutical composition for prophylaxis and/or treatment of thromboembolic diseases.

In a fifth object, the present invention presents the use of sculptin or recombinant protein for prophylaxis or treatment of thromboembolic diseases or as a Direct and specific inhibitor of thrombin.

In a sixth object, the present invention presents an expression vector, gene construct or plasmid comprising the synthetic gene describe in the present invention.

In a seventh object, the present invention presents a method of treatment for prophylaxis of thromboembolic diseases comprising administration of an effective dose of sculptin or recombinant protein of the present invention and/or fragments thereof.

These and other objects of the invention will be promptly appreciated by those skilled in the art and by companies interesting in such area, and they will be described in sufficient details for reproduction in the following description.

BRIEF DESCRIPTION OF FIGURES

FIG. 5 discloses "GKPQG" as SEQ ID NO: 18, "MPKGG" as SEQ ID NO: 19, and "SDAVH" as SEQ ID NO: 20.

FIG. 8 discloses SEQ ID NOS 21-25, respectively, in order of appearance.

DETAILED DESCRIPTION OF THE INVENTION

Figure 1:
FIG. 1 shows phylogenetic analysis of Sculptin. Protein sequences of tick- and leech inhibitors of thrombin were retrieved from database Swiss-Prot/TrEMBL (uniprot.org) and the phylogenetic profile was determined using the Neighbor-Joining method embedded in MEGA 7.0. Bootstrap consensus was 100 and the threshold value for condensed tree was 60% replication of corrupted bootstrap (see, experimental procedures). The access number of each sequence is given and the query position is highlighted in red. A single domain of sculptin was taken into account during the phylogenetic construct.

Herein, a novel class of thrombin inhibitors will be described, particularly direct and specific thrombin inhibitors, which were modified from sculptin identified in transcriptome analysis of tick salivary glands. It consists in 168 residues having four exactly similar repeats and presenting evolving divergence from classic hirudin. Recombinant protein is a competing, specific, and reversible thrombin inhibitor, with K of 18.5±2.2 pM. It is slowly digested by thrombin and loses its inhibitory activity. Accordingly, recombinant protein is hydrolyzed by factor Xa and each polypeptide fragment is able for inhibiting thrombin in independent way. One single domain of recombinant protein retains solely ~45% of inhibitory activity, which was proposed for binding to thrombin in bivalent way. Formation of structure similar to helix/small turn by binding residues of active site from domain of recombinant protein may become it a thrombin inhibitor most potent than hirulogs. In addition, recombinant protein prolongs coagulation through its extrinsic and intrinsic metabolic pathways. It was considered along with data to allow for settling that recombinant protein and independent domain(s) thereof have strong potential for becoming a therapeutic antithrombotic compound or for novel treatment of thromboembolic diseases.

The present invention has the inventive concept common to several objects thereof the inhibitors of thrombin, particularly direct thrombin inhibitors and fragments thereof.

In one first object, the present invention shows a recombinant protein comprising one sequence with at least 60% of identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same. In one embodiment, recombinant protein comprises one sequence with at least 70%, more preferentially at least 90%, more preferentially at least 95%, even more preferentially at least 99% of identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same.

In one embodiment, recombinant protein consists of one sequence with at least 60% of identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same. In one embodiment, recombinant protein consists of one sequence with at least 70%, more preferentially at least 90%, more preferentially at least 95%, even more preferentially at least 99% of identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same.

In one embodiment, recombinant protein comprises one sequence with SEQ ID NO: 1 or SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combinations of the same.

In one embodiment, recombinant protein consists of sequence with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 or combination of the same.

The present invention has as a second object a process for obtaining said recombinant protein and/or fragments thereof from salivary gland cDNA from tick *Amblyoma cajennense*.

In a third object, the present invention shows a synthetic gene comprising one sequence with at least 60% of identity with SEQ ID NO: 17. In one embodiment, synthetic gene comprises one sequence with at least 70%, more preferentially at least 90%, more preferentially at least 95%, even more preferentially at least 99% of identity with SEQ ID NO: 17.

In one embodiment, synthetic gene consists of one sequence with at least 60% of identity with SEQ ID NO: 17. In one embodiment, synthetic gene consists of one sequence with at least 70%, more preferentially at least 90%, more preferentially at least 95%, even more preferentially at least 99% of identity with SEQ ID NO: 17.

In one embodiment, synthetic gene comprises one sequence with SEQ ID NO: 17.

In one embodiment, synthetic gene consists of one sequence with SEQ ID NO: 17.

In a fourth object, the present invention shows the use of sculptin or recombinant protein for preparing a medication or pharmaceutical composition for prophylaxis and/or treatment of thromboembolic diseases.

In a fifth object, the present invention shows the use of sculptin or recombinant protein for prophylaxis and/or treatment of thromboembolic diseases and/or as a direct and specific inhibitor of thrombin.

In a sixth object, the present invention shows an expression vector, gene construct or plasmid comprising the synthetic gene described in the present invention.

In a seventh object, the present invention shows a method for treatment and/or prophylaxis of thromboembolic diseases comprising administration of an effective dose of sculptin or recombinant protein of the present invention and/or fragments thereof.

In context of the present invention, "thromboembolic diseases" may be understood as disorders related to coagulation or blockage of blood vessels, arteries or veins by locally formed clots or by thrombus delivered in systemic circulation, such e.g., thrombosis, heart attack, apoplexy, Angina pectoris (including unstable angina), reocclusions and restenosis following angioplasty or coronary artery bypass, peripheral arterial occlusive diseases, transitory ischemic attacks, pulmonary embolisms, deep vein thrombosis, or disseminated intravascular coagulation (DIC).

Therefore, the invention contributes for health-related areas, novel thrombin inhibitors are disclosed, particularly direct and specific thrombin inhibitors, highly specified, useful in treatment or prophylaxis of thromboembolic diseases.

EXAMPLES—EMBODIMENTS

Examples shown herein aim solely exemplify one from several ways to implement the invention, however without limitation of the scope thereof by no means.

Amino acid sequence of sculptin was identified from analysis of cDNA library of salivary gland from tick *Amblyoma cajennense* (currently *Amblyoma sculptum*).

As from the amino acid sequence identified in library, a reverse translation was performed, through software BLAST-X (NCBI), using table of use of codons from *Escherichia coli*, thus, leading to a coding DNA sequence for recombinant protein, for protein expression in heterologous system (*E. coli* BL21 (DE3).

As from coding nucleotide sequence of sculptin, a synthetic gene was designed (described in SEQ ID NO: 17), incorporating a cleavage site of restriction enzyme NcoI at end 5' and the coding sequence for histidine tail (HIS6) (SEQ ID NO: 26) and a cleavage site of restriction enzyme XhoI at end 3'. Next, synthetic gene sequence was sent to company GenOne Soluções em Biotecnologia (Rio de Janeiro, Brazil) for codon optimization with a proprietary algorithm, gene synthesis and cloning in expression vector for *E. coli*, pET-28a (Novagen, Merck Biosciences, Dramstadt, Germany).

Plasmid synthesized and provided by company GenOne was used for transforming strain of *E. coli* One Shot BL21 (DE3) (Invitrogen, Carlsbad, California, USA) through method with calcium chloride.

10 ng of plasmid pET28a-Sculptin was incubated with 50 µL of competing cell suspension BL21 (DE3) for 30 minutes in ice. Next, cells were undergone to thermal shock by incubation at 42° C. for 30 minutes, followed by incubation in ice for 10 minutes. Afterwards, 1 mL of LB medium was added and the suspension was incubated for one hour at 37° C.

Following the above, cells were plated in solid LB culture medium containing 100 µg/mL of ampicillin and the plate was incubated overnight at 37° C. The next day, a colony was isolated and used for inoculation of LB medium 10 mL containing 100 µg/mL of ampicillin overnight, at 37° C. The next day, glycerol 50% was added to culture, suspension was partitioned in tubes containing 1 mL of suspension and the same were frozen at −80° C., giving rise to master seed lot.

Experiments for expression of recombinant protein in *E. coli* were always started from a bottle of seed lot, inoculating in LB medium containing 100 µg/ml of ampicillin and maintained at 37° C. with stirring of 240 rpm overnight, which composes pre-inoculums.

The next day, a sufficient amount of pre-inoculums was used for inoculating LB culture medium containing 100 µg/mL of ampicillin, in a ratio of 1 volume of pre-inoculums to 100 volumes of culture medium. Culture was maintained at 37° C., with stirring at 240 rpm, during about two hours, up to achieve optic density (OD600) between 0.5-0.6. When such optic density was achieved, IPTG inductor was added in a final concentration of 1 mM, and culture was incubated again at 37° C. for 4 hours.

Following incubation, cells were harvested through centrifugation at 6000 rpm for 30 minutes, and supernatant was discarded when centrifugation ends. Cells were re-suspended in saline solution NaCl (150 mM) in a ratio of 1 mL of solution to every 8 g of wet cell mass (from this step forward the ratio of 1 mL of iced solution for every 8 g of wet mass was used in all processes). Cells were centrifuged again as above and re-suspended in lysis buffer. Lysozyme was added to suspension in a final concentration of 0.25 mg/mL for every cell wall disruption, and incubation was maintained for 30 minutes at 37° C. with stirring at 80 rpm. Next, suspension was undergone to 4 sonication cycles in strength of 70% for cell disruption and fragmentation of genomic DNA.

Suspension was centrifuged at 16000 rpm (4° C.) for one hour in order to split insoluble material from soluble material.

Recombinant protein (SEQ ID NO: 1) was expressed in bacterium cytoplasm, thus, soluble fraction was used for purifying protein, which contains histidine tail through affinity chromatography, using chromatography system AKTA AVANT (GE Healthcare, Chicago, Illinois, USA) and column HisTrap FF. Soluble material was applied in column, thus immobilizing the recombinant protein. Following, washing was performed with 10 CV (column volumes) of lysis buffer. Protein elution was performed through linear gradient (10 CV) from zero to 100% of buffer B. Harvested fractions containing partially purified protein were undergone to buffer exchange in desalting column (HiPrep 26/10) and one second purification step of recombinant protein was performed through ion exchange chromatography in column CaptoQ, using the same washing and elution steps through linear gradient described above. Fractions containing the purified protein were combined in a pool and buffer exchange to PBS buffer was performed through desalting column (HiPrep 26/10).

Recombinant protein (SEQ ID NO: 1) in pure form obtained through such process was used in all experiments described herein.

Analysis of Sculptin Sequence and Phylogeny

Figure 8:
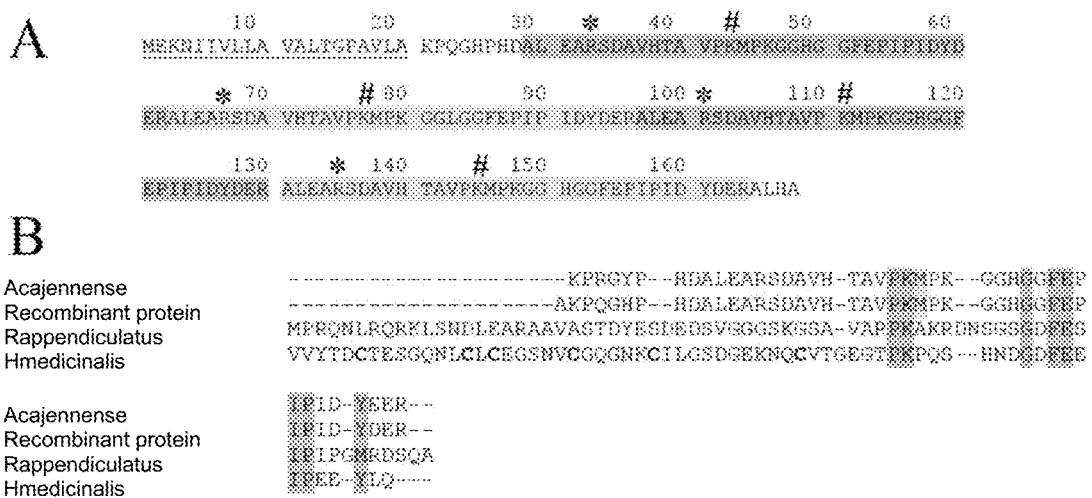
FIG. 8 shows an analysis of protein sequence. (A) recombinant protein sequence modified from sculptin, in whose transcriptome analysis of tick salivary gland was identified. Assumed peptide signal is underlined. Four peptide iterations within recombinant protein are shown by alternated grey and yellow colors. (B) Multiple alignment of recombinant protein with hirudin from *Amblyomma cajennense*, *Rhipicephalus appendiculatus* and *Hirudo medicinalis*. Conserved residues are highlighted in grey. Hirudin PKP-linked active site from *Hirudo medicinalis* is modified to PKM in sculptin. Cleavage sites of factor Xa and thrombin are identified through asterisk and hash mark, respectively.

Sculptin sequence was identified in transcriptome profile from salivary glands of *Amblyomma cajennense*. Sculptin, a 168 amino acid polypeptide consists of one single peptide, and four exactly similar repeats of 34 amino acids (FIG. 8A). Multiple alignment of classic hirudin from medicinal leech presented only few similarities and even residues linked to thrombin active site were not preserved. The phylogenetic analysis from a domain of single sculptin repeat to other serine protease inhibitors suggested that it shares a common predecessor with variants of leech hirudin, but it is different regarding evolving time. In fact, in evolving tree, sculptin was closer to serine protease inhibitors from antistassin family, i.e., hirustasin, guamerin, bdellastasin, theromin and therostasin, than classic hirudin from leech. As expected, sculptin belongs to the same sequence family similar to those from tick hirudin (FIG. 1).

Purification of Recombinant Protein

Figure 9:
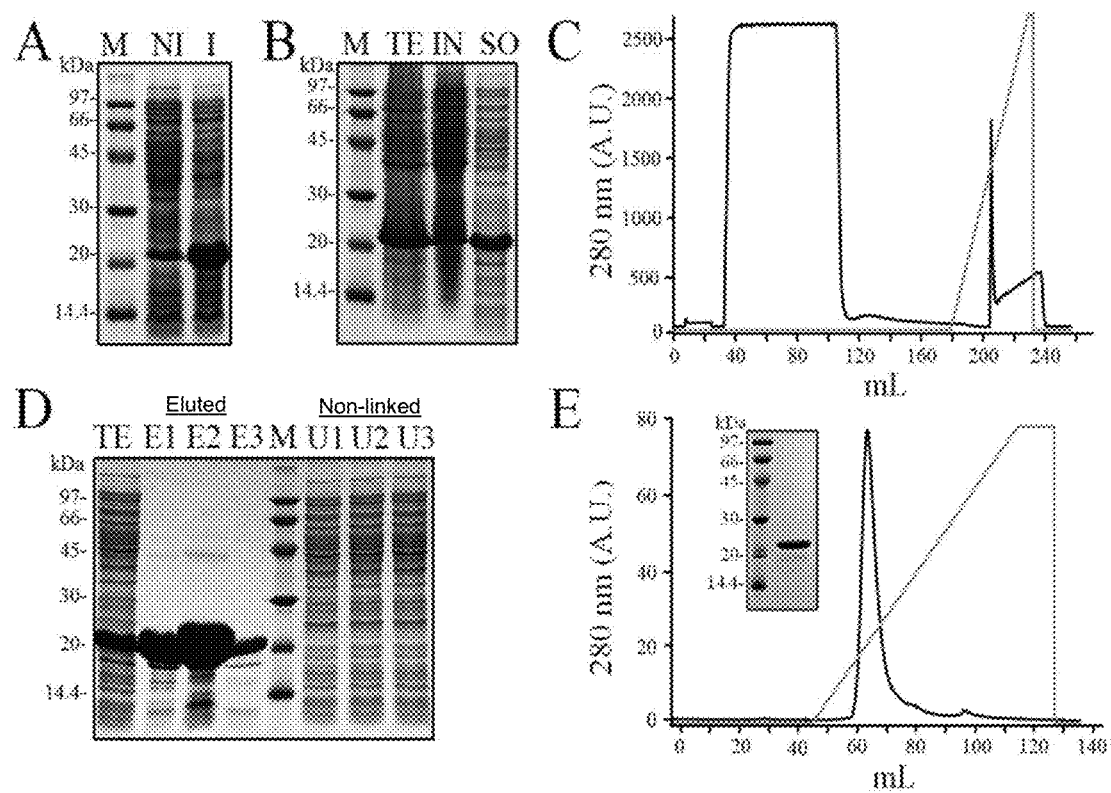
FIG. 9 shows expression and purification of recombinant protein. Synthetic gene of recombinant protein was cloned into expression vector pET28a and recombinant protein was expressed in *E. coli* BL21 (DE3) in liquid medium at 37° C. Whole cell lysates from both no induced or induced cultures (IPTG 0.5 mM) were analyzed through SDS-PAGE (15%). (A) Induction SDS-PAGE of recombinant protein. Strip M, NI and I represent protein marker, non IPTG induced, respectively. (B) SDS-PAGE of cell lysate from *E. coli* following recombinant protein expression. Strips M, TE, IN, SO correspond to protein marker, full extract, insoluble and soluble fractions, respectively. (C) Purification by affinity chromatography of recombinant protein. Soluble fraction was filtered through a 0.45 µm membrane and applied in Ni chelating affinity column of His tag. Linked protein was eluted with imidazole and 15 µl from each fraction was analyzed from SDS-PAGE. (D) SDS-PAGE from affinity chromatography fractions. Strips TE, E, M and U represent full extract, fractions of eluted protein, protein marker and non-linked protein fraction respectively. (E) Purification of recombinant protein through Ion exchange chromatography. Inserted image showing SDS-PAGE from strip of purified recombinant protein.
Figure 10:
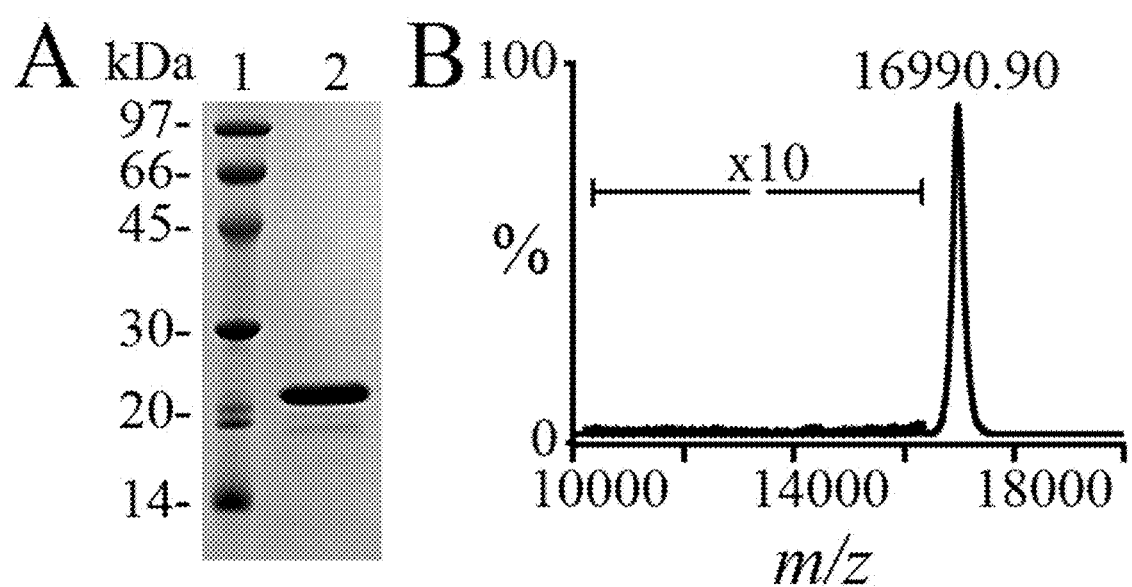
FIG. 10 shows purification of recombinant protein, a thrombin-specific inhibitor. (A) SDS-PAGE from purified recombinant protein using conventional chromatographic methods (see experimental procedures and FIG. S2). (B) MALDI-TOF MS spectrum from purified recombinant protein.

Synthetic construct of recombinant protein without signal peptide and with one polyhistidine tail C-terminal was cloned into expression vector pET28a. Recombinant protein was well expressed and was present mainly in soluble fraction (FIG. 9). Recombinant protein was purified by conventional affinity and ion exchange chromatography (FIG. 9). Analysis by mass spectrometry indicated a mass of 16990.90 Da for recombinant protein (SEQ ID NO: 1) in purified form, however in SDS-PAGE, it is performed just above the marker strip of 20 kDa (FIGS. 10A and 10B). Purified recombinant protein was used for additional experiments (image inserted in FIG. 2A).

Recombinant Protein is a Thrombin-Specific Inhibitor

Figure 2:
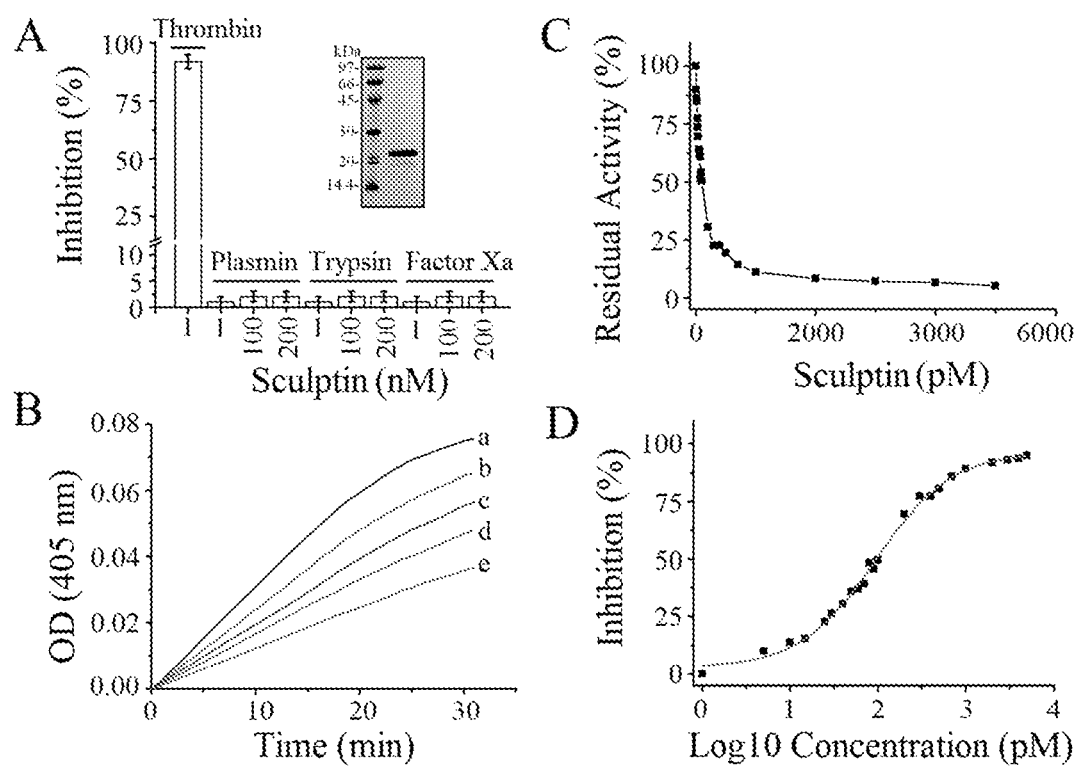
FIG. 2 shows the specificity of recombinant protein for thrombin and its dose dependency, and $IC_{50}$ for inhibiting thrombin. (A) Inhibition of serine proteases through recombinant protein. Serine protease (100 pM; thrombin, plasmin, trypsin or factor Xa) was incubated with recombinant protein (1, 100 and 200 nM) in phosphate buffer 50 mM containing NaCl 150 mM and 0.1% of PEG 6000, pH 7.4 for 6 h at 37° C. Following addition of chromogenic substrate corresponding to reaction mixture, hydrolysis thereof was monitored at 405 nm. For factor Xa activity, buffer contained phosphatidylserine and phosphatidylcholine 50 μM. Illustration presented in (A) shows the SDSPAGE of purified recombinant protein (SEQ ID NO: 1), which was used in experiments. (B) Typical curves for hydrolysis of chromogenic substrate S-2238 (15 μM) by thrombin 0.1 nM in absence (trace a) or presence of recombinant protein (trace b, 15 pM; trace c, 30 pM; trace d, 60 pM and trace e, 100 pM) in phosphate buffer 50 mM containing NaCl 150 mM and 0.1% of PEG 6000, pH 7.4 at 37° C. (C) Residual activity of thrombin in presence of increasing concentration of recombinant protein. (D) Dose-response curves for thrombin inhibition by recombinant protein. Percentage of thrombin inhibition was plotted versus the concentration record of recombinant protein. Experimental condition of (C) and (D) is the same as in (B).

The first performed experiment was the test of serine proteases inhibition through recombinant protein. For this purpose, thrombin, trypsin, plasmin and factor Xa were chosen. Hydrolysis of a chromogenic substrate through serine proteases in the presence and absence of recombinant protein was monitored in a spectrophotometer way. Recombinant protein in concentration of 1 nM decreases the residual activity of thrombin in about 97% (FIG. 2A). For the other hand, recombinant protein (1, 100, 200 nM) did not inhibit factor Xa, trypsin and plasmin (FIG. 2A).

Figure 3:
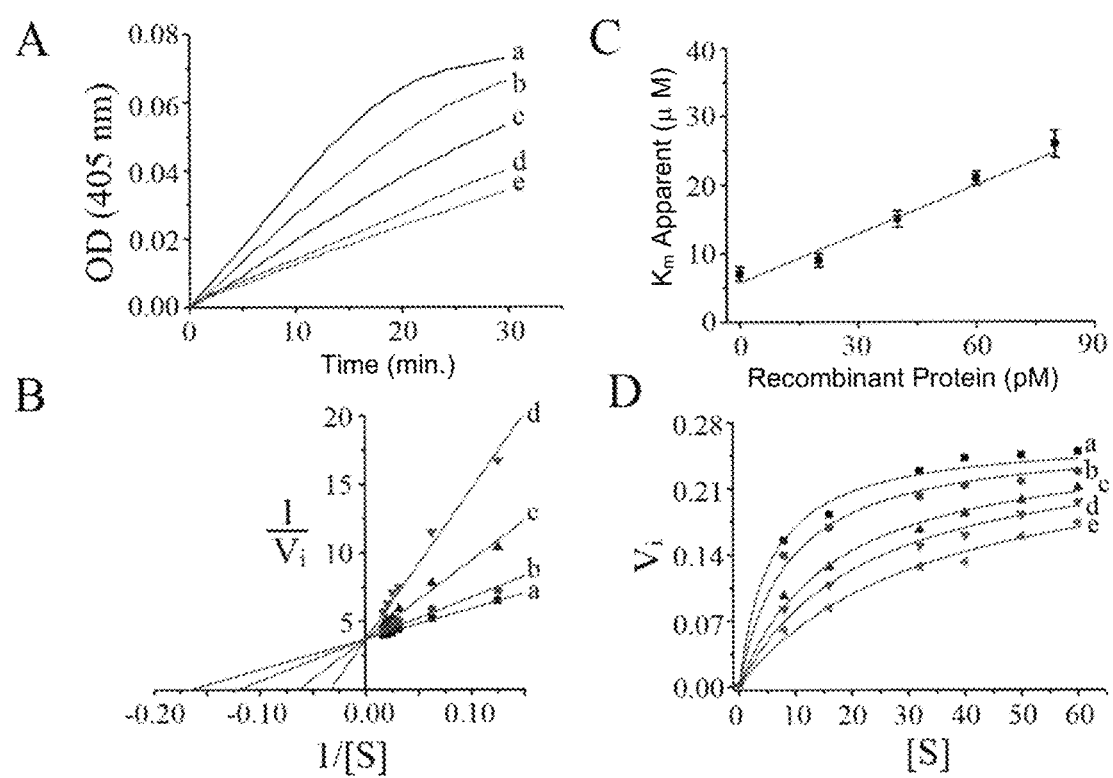
FIG. 3 shows thrombin inhibition kinetics by recombinant protein. (A) Typical progress curves for hydrolysis of chromogenic substrate S-2238 by thrombin 0.1 nM in absence (trace a) and presence of recombinant protein (trace b, 20 pM; trace c, 40 pM; trace d, 60 pM and trace e, 80 pM) in phosphate buffer 50 mM containing NaCl 150 mM and 0.1% of PEG 6000, pH 7.4 at 37° C. Reactions were started by addition of thrombin to mixture containing recombinant protein and S-2238. (B) Lineweaver-Burk plot for thrombin inhibition by recombinant protein using Eq. (1). Reciprocation of initial speed of thrombin inhibition in absence (trace a) and presence of recombinant protein (trace b, 20 pM; trace c, 40 pM and trace d, 60 pM) in differing substrate concentrations. (C) Perceived Km obtained from (B) was plotted versus respective concentration for obtaining Ki. (D) Nonlinear regression for competing inhibition using Eq. (2). Initial speed of thrombin inhibition in absence (trace a) and presence of recombinant protein (trace b, 20 pM; trace c, 40 pM; trace d, 60 pM and trace e, 80 pM) in differing substrate concentrations. Experimental condition of (B), (C) and (D) is the same as of (A).

Inhibition of Thrombin Residual Activity by Recombinant Protein and Calculation of $IC_{50}$ Value Thrombin was the sole enzyme inhibited by recombinant protein. Additionally, thrombin inhibition was analyzed with increasing concentrations of recombinant protein. Data rendered that the increase of a concentration of recombinant protein decreased residual activity of thrombin (FIG. 2B-D). Percentage plot of inhibition versus concentration log was adjusted in dose-response function of equation 1 and $IC_{50}$ value of 86.6±1.9 pM was calculated (FIG. 3D).

Kinetics Thrombin Inhibition by Recombinant Protein

Figure 4:
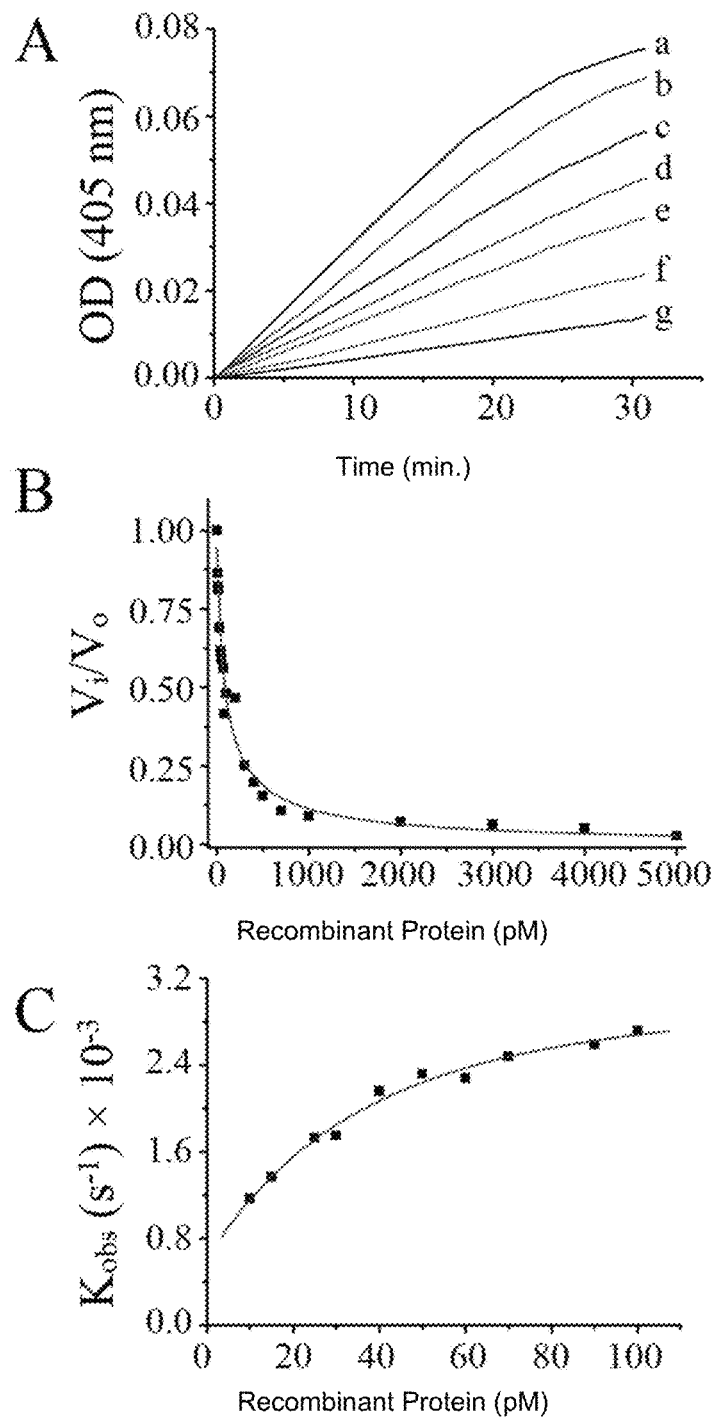
FIG. 4 shows the relation between apparent first order rate and concentration of tight binding inhibitor of recombinant protein. (A) Typical progress curves for hydrolysis of chromogenic substrate S-2238 15 µM by thrombin 0.1 nM in absence (trace a) and presence of recombinant protein (trace b, 10 pM; trace c, 30 pM; trace d, 70 pM; trace e, 100 pM; trace f, 200 pM and trace g, 500 pM) in phosphate buffer 50 mM containing NaCl 150 mM and 0.1% of PEG 6000, pH 7.4 at 37° C. Reactions were started through thrombin addition to mixture containing recombinant protein and S-2238. (B) Equilibrium rate of thrombin regarding to concentration of recombinant protein (C) Calculation of constant off-rate. Constant of apparent first order rate was calculated using a nonlinear regression adjustment, where crossing and slope are kon and koff respectively. Experimental condition of (B) and (C) is the same of (A).

In order to assess the inhibition type performed by recombinant protein in thrombin, kinetics parameters of chromogenic substrate S-2238 hydrolysis by thrombin in presence of recombinant protein were determined. For this purpose, several tests were performed using (i) a fixed substrate concentration and increasing concentrations of recombinant protein; and (ii) a fixed concentration of recombinant protein and increasing concentrations of S-2238. Typical hydrolysis curves of S-2238 by thrombin are given in FIG. 3A. Initial speed of chromogenic substrate S-2238 hydrolysis by thrombin in presence of recombinant protein was adjusted to Lineweaver-Burk plots using equation 2. Lineweaver-Burk plots suggest a constant Vmax and changes in Km compared to reaction in absence of recombinant protein, which is a characteristic of competing inhibition (FIG. 3B). Apparent Km for each inhibitor concentration was plotted versus respective inhibitor concentration and Ki was calculated using equation 3. Ki value obtained was 18.5±2.2 pM of recombinant protein for thrombin inhibition (FIG. 3C) and it was even confirmed by data adjustment to nonlinear regression for competing enzyme inhibition using equations 3 and 4 (FIG. 3D). Ki value of 18.1±1.7 pM obtained through this method was similar to that calculated previously (FIG. 4D).

Binding Kinetics of Recombinant Protein to Thrombin

For binding kinetics, pre-mixed substrate and recombinant protein concentrations were added to reaction mixtures already containing thrombin (see experimental procedure). Traces of inhibition are straight and separate lines right from the beginning of reaction, thus suggesting fast and tight binding between recombinant protein to thrombin (FIG. 4A). In addition, fractional speeds were plotted versus inhibitor concentrations using equation 5 of Morrison tight binding and data is best suited in equation (FIG. 4B). Ki of 19.5±3.5 pM was calculated by equation of Morrison tight binding, which was similar to that determined by nonlinear regression for competing enzyme inhibition. Further, $K_{obs}$ calculated using equation 6 was plotted versus recombinant protein concentration. From the plot, $K_{on}$ and $K_{off}$ were calculated which resulted in 4.04±0.03×10$^7$ M$^{-1}$ s$^{-1}$ and 0.65±0.04×10$^{-3}$ s$^{-1}$ respectively (FIG. 4C). Inhibition constant (Ki) of 16.1±1.4 pM was calculated using equation 7.

Degradation of Recombinant Protein by Serine Proteases

Figure 5:
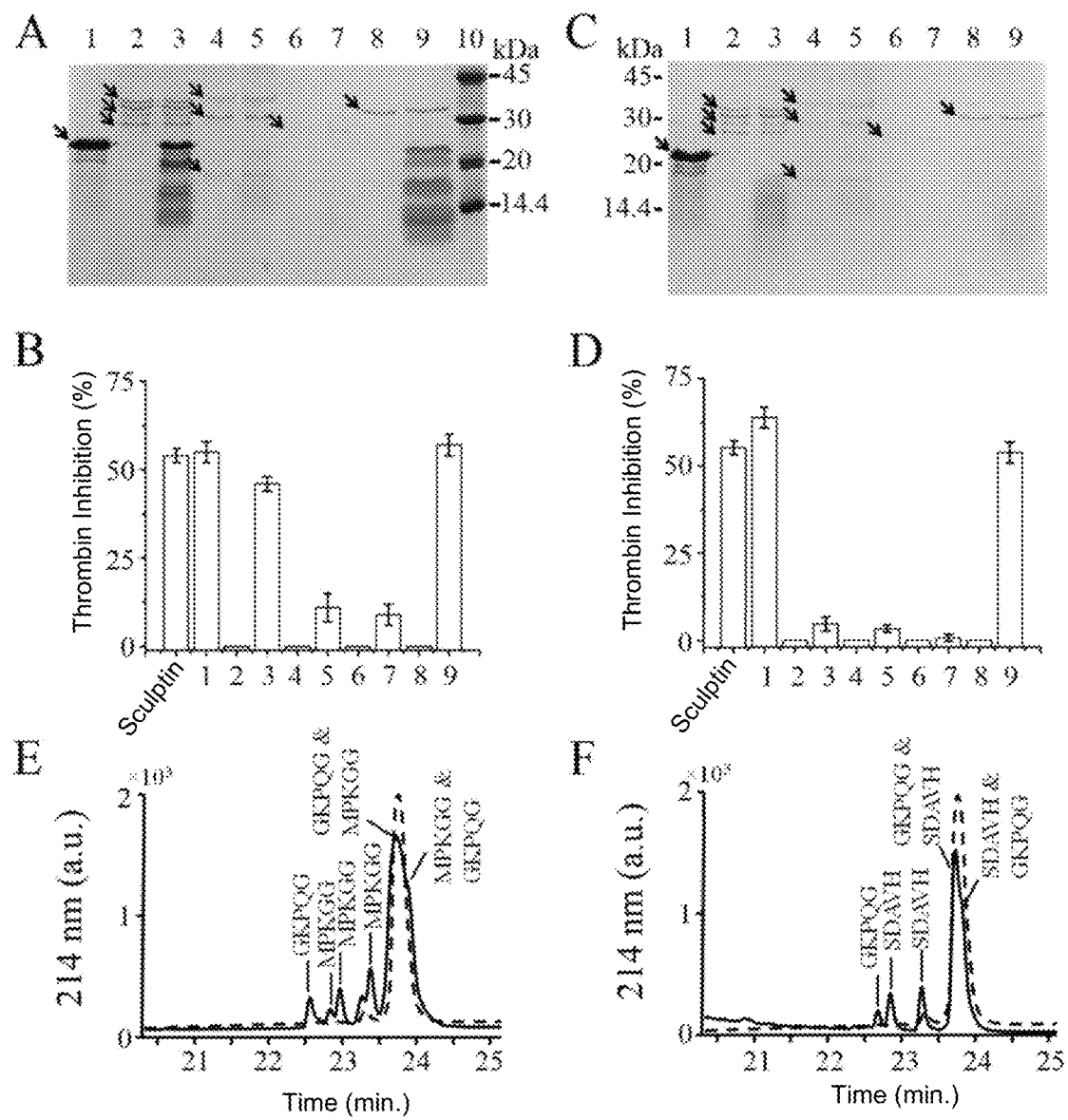
FIG. 5 shows degradation of recombinant protein by serine proteases and its activity of thrombin inhibition. Recombinant protein (10 µM) was incubated with or without serine protease 1 µM (thrombin, plasmin, trypsin or factor Xa) in phosphate buffer 50 mM containing NaCl 150 mM and 0.1% of PEG 6000, pH 7.4 for 4, 6, 7 or 18 h at 37° C. Reaction mixtures (20 µl) were split by SDS-PAGE. (A) hydrolysis SDS-PAGE (15%) of recombinant protein by serine proteases following 6 h of incubation. (B) Percentage of thrombin inhibition by recombinant protein following 6 h of incubation with serine protease (see experimental procedures). (C) hydrolysis SDS-PAGE (15%) of recombinant protein by serine proteases following 18 h of incubation. (D) Percentage of thrombin inhibition by recombinant protein following 18 h of incubation with serine protease (see experimental procedures). Numbering of (B) and (D) corresponds to numbering of (A) and (C), respectively, and recombinant protein control is represented by CTRL. Recombinant protein (strip 1); thrombin (strip 2) and thrombin with recombinant protein (strip 3); plasmin (strip 4) and plasmin with recombinant protein (strip 5); trypsin (strip 6) and trypsin with recombinant protein (strip 7); factor Xa (strip 8) and factor Xa with recombinant protein (strip 9) and protein marker (strip 10; in A). (E) Identification of cleavage sites of thrombin in recombinant protein following 7 h of incubation. (F) Identification of cleavage sites of factor Xa in recombinant protein following 4 h of incubation. Cleavage sites of thrombin and factor Xa in recombinant protein sequence are shown in FIGS. S1 and S2, respectively. Experimental procedure for (C), (D), (E) and (F) was the same as for (A) and (B), except the incubation time and the type of serine protease used.

Afterwards, it was determined whether serine proteases, like thrombin, plasmin, factor Xa and trypsin, hydrolyze recombinant protein. For this purpose, recombinant protein (10 µM) was incubated with or without serine protease 1 µM (thrombin, plasmin, trypsin or factor Xa) in phosphate buffer 50 mM containing NaCl 150 mM and 0.1% of PEG, pH 7.4 for 6 h or 18 h at 37° C. SDS-PAGE of reaction mixture following 6 h of incubation presented that, compared to control strip of recombinant protein, strip intensity of 20-kDa (corresponding to non-digested recombinant protein) decreased and strips of lower molecular weight appeared in recombinant protein incubated by thrombin (FIG. 5A). For the other hand, following 6 h of incubation, strip of 20-kDa completely disappeared in recombinant protein incubated by plasmin and trypsin (FIG. 5A). Accordingly, following the same incubation time, factor Xa also converted the recombinant protein in fragments (FIG. 5A). For the test of thrombin inhibition, the same samples were diluted 100 thousand times for a final concentration of recombinant protein of 100 pM and reaction mixtures were further supplemented with thrombin 100 pM. Upon addition of chromogenic substrate S-2238, the hydrolysis thereof by thrombin was monitored in spectrophotometer way. Data reveal that recombinant protein incubated without serine protease for 6 h inhibited thrombin in similar way to control (control is 100 pM of fresh recombinant protein; FIG. 5B). For the other hand, recombinant protein incubated with thrombin presented its inhibitory activity decreased by 20% and recombinant protein incubated for 6 h with plasmin or trypsin presented its inhibitory activity decreased by 80% (FIG. 5B). Interestingly, recombinant protein digested with factor Xa retained its thrombin inhibition activity (FIG. 5B). Afterwards, recombinant protein incubated with serine proteases for 18 h was examined. Strip of 20-kDa, corresponding to recombinant protein monomer, completely disappeared from reaction mixtures of recombinant protein incubated with serine protease (FIG. 5C). In the same way, for test of thrombin inhibition, samples were diluted 100 thousand times and they were further supplemented with thrombin 100 pM. As expected, recombinant protein incubated without serine protease for 18 h inhibited thrombin in similar way to control of fresh recombinant protein (FIG. 5D). However, recombinant protein incubated with thrombin, plasmin and trypsin did not inhibit thrombin (FIG. 5D). Interestingly, recombinant protein incubated by factor Xa even inhibited the thrombin activity (FIG. 5D).

Sequencing N-Terminal of Recombinant Protein Hydrolyzed by Thrombin

As discussed above, thrombin degrades recombinant protein. Hereinafter, our next step was to determine cleavage sites of thrombin in recombinant protein sequence. For this purpose, recombinant protein was incubated with thrombin for 7 h and peptides generated during hydrolysis were split by reverse phase chromatography. Individual peaks were gathered and undergone to Edman N-terminal sequencing. Sequenced residues for the first peak were GKPQG (SEQ ID NO: 18), being the first five residues of recombinant protein (FIG. 5E). Sequenced residues for the following three peaks ($2^{nd}$, $3^{rd}$, and $4^{th}$) were MPKGG (SEQ ID NO: 19), being basically N-terminal residues of recombinant protein peptides generated by thrombin (FIG. 5E). The last peak ($5^{th}$) with a retention time equal to control was sequenced for having residues of MPKGG (SEQ ID NO: 19) and GKPQG (SEQ ID NO: 18) in N-terminal, suggesting that this peak has preserved and partially degraded recombinant protein (FIG. 5E). Fractions were also undergone to mass spectrometry, and they were in accordance with data from Edman sequencing (Table 1). Theoretical and experimental masses of peptides are listed on table 1.

TABLE 1

Recombinant protein fragments generated by thrombin.

| Peak number[a] | Recombinant protein fragment [b] | Theoretical Mass [MH]+ | Calculated Mass[c] [MH]+ |
|---|---|---|---|
| H1 | GKPQGHPHDALEARSDAVHTAVPK (SEQ ID NO: 2) | 2518.77 | 2521.74 |
|  | GKPQGHPHDALEARSDAVHTAVPKMPK GGHGGFEPIPIDYDERALEARSDAVHTAV PK (SEQ ID NO: 3) | 6162.85 | 6169.56 |
| H2 | MPKGGHGGFEPIPIDYDERALEARSDAVH TAVPK (SEQ ID NO: 4) | 3663.09 | 3663.90 |
| H3 | MPKGGHGGFEPIPIDYDERALHALEHHHH HH (SEQ ID NO: 5) | 3572.92 | 3572.70 |
| H5 | MPKGGHGGFEPIPIDYDERALEARSDAVH TAVPKMPKGGHGGFEPIPIDYDERALHAL EHHHHHH (SEQ ID NO: 6) | 7217.00 | 7202.66 |
| H6 | MPKGGHGGFEPIPIDYDERALEARSDAVH TAVPKMPKGGLGGFEPIPIDYDERALEAR SDAVHTAVPK (SEQ ID NO: 7) | 7282.19 | 7261.19 |
|  | MPKGGLGGFEPIPIDYDERALEARSDAVH TAVPKMPKGGHGGFEPIPIDYDERALEAR SDAVHTAVPKMPKGGHGGFEPIPIDYDER ALHALEHHHHHH (SEQ ID NO: 8) | 10837.10 | 10807.97 |
|  | MPKGGHGGFEPIPIDYDERALEARSDAVH TAVPKMPKGGLGGFEPIPIDYDERALEAR SDAVHTAVPKMPKGGHGGFEPIPIDYDER ALEARSDAVHTAVPKMPKGGHGGFEPIPI DYDERALHALEHHHHHH (SEQ ID NO: 9) | 14481.18 | 14431.37 |
|  | GKPQGHPHDALEARSDAVHTAVPKMPK GGHGGFEPIPIDYDERALEARSDAVHTAV PKMPKGGLGGFEPIPIDYDERALEARSDA VHTAVPKMPKGGHGGFEPIPIDYDERALE ARSDAVHTAVPKMPKGGHGGFEPIPIDYD ERALHALEHHHHHH (SEQ ID NO: 1) | 16981.94 | 16990.90 |

Recombinant protein (10 μM) was incubated with thrombin 1 μM in phosphate buffer 50 mM containing NaCl 150 mM and 0.1% of PEG 6000 pH 7.4 for 4 h at 37° C. Reaction mixtures were split by reverse phase HPLC column C-18. Fractions were undergone to Edman sequencing or mass spectrometry MALDI-TOF.

Sequencing of N-Terminal of Recombinant Protein Hydrolyzed by Factor Xa

Cleavage sites of factor Xa in recombinant protein were also determined. Peptides generated by incubation of recombinant protein with factor Xa for 4 h were split by reverse phase chromatography. Edman sequencing presented that N-terminal residues for the first peak were GKPQG (SEQ ID NO: 18), being the first five residues of recombinant protein (FIG. 5F). Sequenced residues for the next two peaks (2nd and 3rd) were SDAVH (SEQ ID NO: 20), which are in fact N-terminal residues of recombinant protein peptides generated by factor Xa (FIG. 5F). The last peak (4th) with retention time equal to control was sequenced to have N-terminal residues MPKGG (SEQ ID NO: 19) and SDAVH (SEQ ID NO: 20), suggesting that this peak has preserved and partially degraded recombinant protein (FIG. 5F). Next, gathered peaks were undergone to mass spectrometry, which were in accordance with data from Edman sequencing (Table 2). Theoretical and experimental masses of peptides are listed on table 2.

TABLE 2

Recombinant protein fragments generated by factor Xa.

| Peak number | Recombinant protein fragmentation | Theoretical Mass | Calculated Mass |
|---|---|---|---|
| H1 | GKPQGHPHDALEARSDAVHTAVPKM PKGGHGGFEPIPIDYDERALEAR (SEQ ID NO: 10) | 5156.74 | 5153.57 |
| H2 | SDAVHTAVPKMPKGGHGGFEPIPIDY DERALEAR (SEQ ID NO: 11) | 3663.10 | 3667.50 |
|  | SDAVHTAVPKMPKGGHGGFEPIPIDY DERALHALEHHHHHH (SEQ ID NO: 12) | 4579.05 | 4582.40 |
| H3 | SDAVHTAVPKMPKGGHGGFEPIPIDY DERALEARSDAVHTAVPKMPKGGHG GFEPIPIDYDERALHALEHHHHHH (SEQ ID NO: 13) | 8223.13 | 8220.55 |
|  | SDAVHTAVPKMPKGGHGGFEPIPIDY DERALEARSDAVHTAVPKMPKGGHG GFEPIPIDYDER (SEQ ID NO: 14) | 6765.55 | 6770.60 |

TABLE 2-continued

Recombinant protein fragments generated by factor Xa.

| Peak number | Recombinant protein fragmentation | Theoretical Mass | Calculated Mass |
|---|---|---|---|
| H4 | SDAVHTAVPKMPKGGHGGFEPIPIDY DERALEARSDAVHTAVPKMPKGGHG GFEPIPIDYDERALEAR (SEQ ID NO: 15) | 7306.17 | 7299.61 |
| | GKPQGHPHDALEARSDAVHTAVPKM PKGGHGGFEPIPIDYDERALEARSD AVHTAVPKMPKGGLGGFEPIPIDYD ERALEARSDAVHTAVPKMPKGGHGG FEPIPIDYDERALEAR (SEQ ID NO: 16) | 12420.90 | 12427.54 |
| | GKPQGHPHDALEARSDAVHTAVPKM PKGGHGGFEPIPIDYDERALEARSD AVHTAVPKMPKGGLGGFEPIPIDYD ERALEARSDAVHTAVPKMPKGGHGG FEPIPIDYDERALEARSDAVHTAVP KMPKGGHGGFEPIPIDYDERALHAL EHHHHHH (SEQ ID NO: 1) | 16981.94 | 16990.90 |

Recombinant protein (10 μM) was incubated with factor Xa 1 μM in phosphate buffer 50 mM containing NaCl 150 mM and 50 μM de PS/PC pH 7.4 for 4 h at 37° C. Reaction mixtures were split by reverse phase HPLC column C-18. Fractions were undergone to Edman sequencing or mass spectrometry MALDI-TOF.

Figure 6:
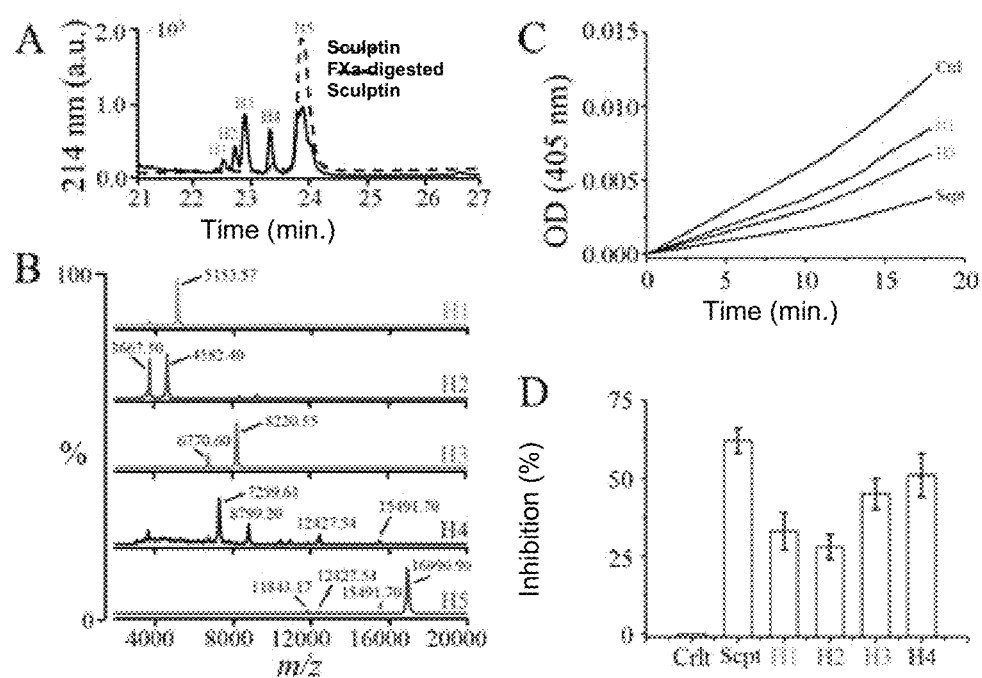
FIG. 6 shows thrombin inhibition activity of recombinant protein fragments generated by factor Xa. Recombinant protein (10 µM) was incubated with or without factor Xa 1 µM in phosphate buffer 50 mM containing NaCl 150 mM, and phosphatidylserine and phosphatidylcholine 50 µM, pH 7.4 for 18 h at 37° C. (A) Reaction mixtures were split through reverse phase HPLC column C-18. (B) Gathered peaks (H1-H5) were subjected to MALDI-TOF MS and thrombin inhibition test (see table 1, for correspondent peptide sequence). (C) Typical progress curves for hydrolysis of chromogenic substrate S-2238 15 µM by thrombin 0.1 nM in absence (trace Ctrl) and presence of recombinant protein fragment 100 pM (traces H1 and H3) or preserved recombinant protein (trace Scpt) in phosphate buffer 50 mM containing NaCl 150 mM and 0.1% of PEG 6000, pH 7.4 at 37° C. (D) Percentage of thrombin inhibition by recombinant protein and fragments thereof. Reaction conditions of percentage of thrombin inhibition were obtained from (C).
Figure 7:
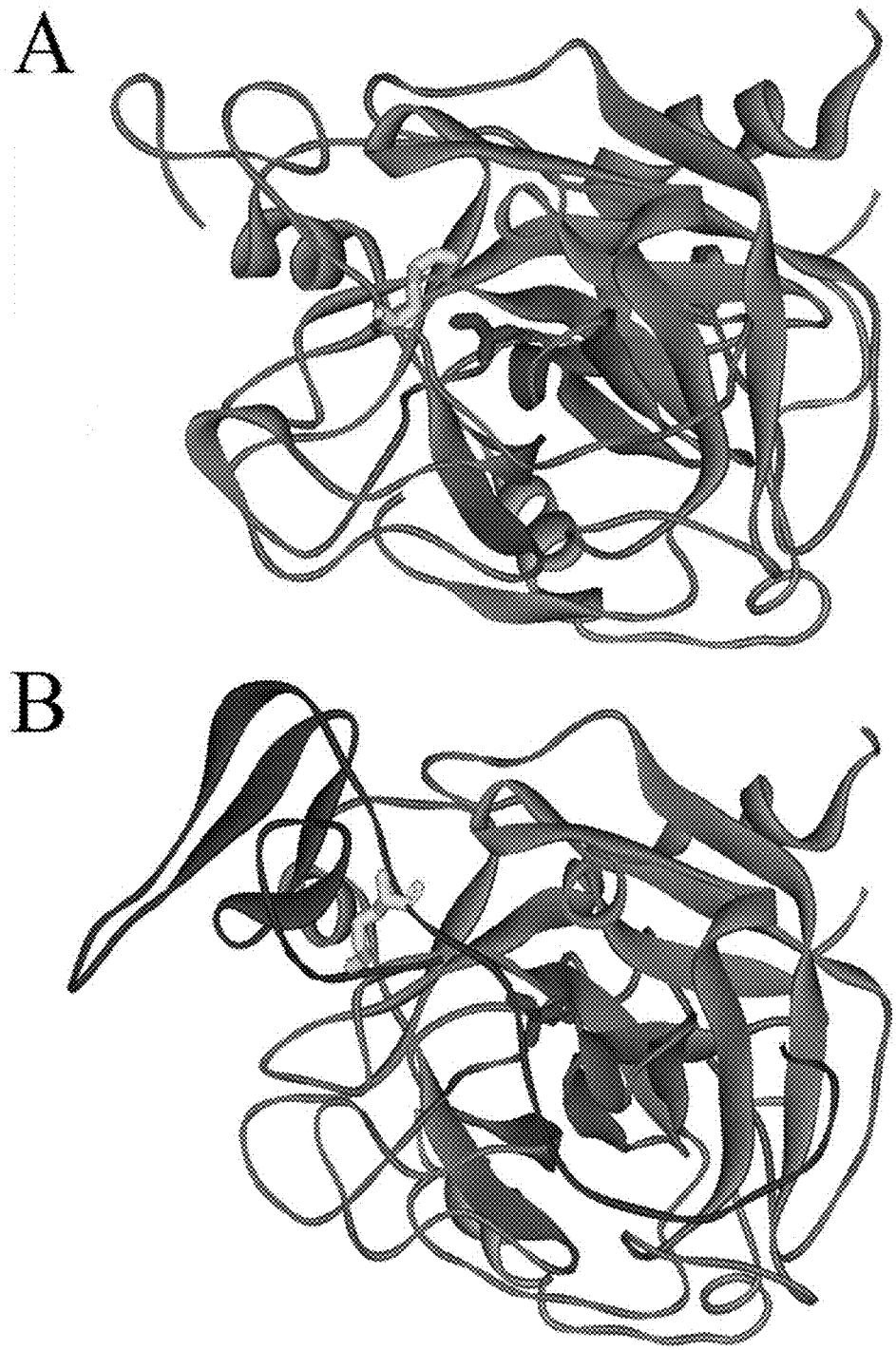
FIG. 7 shows a representative design (Solid strip) of thrombin-linked recombinant protein and hirudin. Brown and cyan colors represent heavy and light chain of thrombin respectively. (A) Recombinant protein in green linked to thrombin (B) Hirudin in blue linked to thrombin. Residue lys from inhibitors is shown in yellow and residue of Ser195 from thrombin active site is shown in red.

Recombinant Protein Fragments Generated by Factor Xa Retain Thrombin Inhibition Activity In addition, recombinant protein was incubated with factor Xa for 18 h and resulting peptides were split by reverse phase chromatography (FIG. 6A). Peaks (named as H1, H2, H3 H4 and H5) were gathered and undergone to mass spectrometry MALDI-TOF (FIG. 6B). In accordance with analysis of mass spectrometry, H1 corresponds to average mass of 5153.57 Da, H2 corresponds to average mass of 3667.50 Da and 4582.40 Da and H3 corresponds to average mass of 8220.55 Da and 6770.60 Da. Similarly, H4 corresponds to average mass of 7299.61 Da and 12427.54 Da and H5 corresponds to 16990.90, 12427.54 Da and 11843.17 Da (FIG. 6B, Table 1). Further, fractions (H1, H2, H3 and H4) were undergone to test of thrombin inhibition (FIG. 6C). Fractions H1, H2, H3 and H4 retained thrombin inhibition activity of about 50%, 45%, 70% and 80% respectively, of preserved no hydrolyzed recombinant protein (FIG. 6D). Peak H5 had mainly preserved recombinant protein, thus it was not considered for test of thrombin inhibition.

The Effect of Recombinant Protein in aPTT, PT and TT

Figure 11:
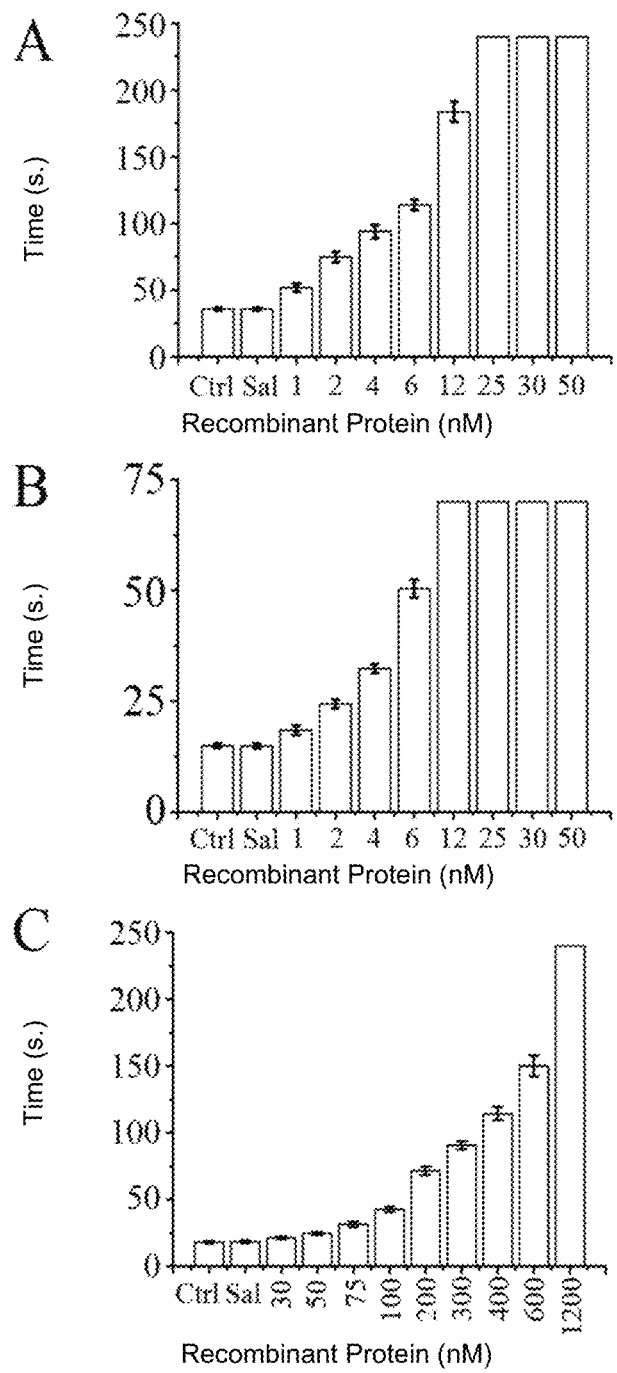
FIG. 11 shows APTT, PT and TT assessment in vitro in isolated human plasma incubated with differing concentrations of recombinant protein. Plasma was obtained from blood of healthy human volunteer and incubated with different concentrations of recombinant protein. APTT, PT and TT were determined like experimental procedure. (A) Activated partial thromboplastin time (B) prothrombin time and (C) thrombin time. Ctrl is related to plasma and Sal is related to plasma plus saline.

Finally, PT, aPTT and TT were assessed in isolated plasma of healthy human volunteers following incubation with recombinant protein for 3 min. at 37° C. Data shows that aPTT and PT were prolonged by recombinant protein in concentration-dependent way (FIGS. 11A and 11B). Maximum test reading for aPTT was achieved following 12 nM, while for PT that was achieved following 6 nM of recombinant protein (FIGS. 11A and 11B). For the other hand, TT was prolonged by recombinant protein in peak-molar range (FIG. 11C).

TABLE 3

Comparison of biochemical proprieties of thrombin inhibitors.

| Inhibitor[a] | Inhibition Type | $K_i$ Value | Administration | Half-life[b] | Ref. |
|---|---|---|---|---|---|
| Recombinant Hirudin[d] | Competing | 19 ± 2 pM | Intravenously | 1.3 h | [11,12] |
| Sulfo-hirudin[d] | Competing | 1.2 ± 0.2 pM | ND | ND | [26,43] |
| Hirugen[d] | No competing | 1.3 ± 0.2 μM | ND | ND | [24] |
| Bivalirudin[d] | No competing | 1.9 ± 2.6 nM | Intravenously | 25 min | [13,25,26] |
| Argatroban | No competing | 39 ± 2 nM | Intravenously | 50 min | [23] |
| Recombinant protein | Competing | 18.5 ± 2.2 pM | ND | ND 8 h[c] | This study |

[a] Direct thrombin inhibitors
[b] Half-life in plasma in healthy human volunteers.
[c] Half-life in plasma ex vivo and in phosphate buffer 50 mM containing 1 μM de thrombin, recombinant protein 10 μM and NaCl 150 mM and 0.1% of PEG 6000 pH 7.4 for 4 h at 37° C.
ND, not determined
[d] Inhibitor of bivalent Thrombin, occupying active site and exosite 1.
[e] The proposed one may be bivalent (single domain) or trivalent (preserved molecule)

Those skilled in the art will appreciate the teachings presented herein and may reproduce the invention in presented models and in other variants, embraced within the scope of attached claims.

What is claimed is:

1. A method for prophylaxis and/or treatment of thromboembolic diseases in a subject in need thereof, comprising administering to said subject an effective dose of a medication or pharmaceutical composition comprising a recombinant protein comprising one sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, wherein the medication or pharmaceutical composition is utilized for prophylaxis and/or treatment of thromboembolic diseases.

2. A method for prophylaxis and/or treatment of thromboembolic diseases and/or as a direct and specific thrombin inhibitor in a subject in need thereof, comprising administering to said subject an effective dose of a medication or pharmaceutical composition comprising a recombinant protein comprising one sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 for prophylaxis and/or treatment of thromboembolic diseases and/or as a direct and specific thrombin inhibitor.

* * * * *